US008486663B2

(12) United States Patent
Paciotti et al.

(10) Patent No.: US 8,486,663 B2
(45) Date of Patent: *Jul. 16, 2013

(54) COMPOSITIONS AND METHODS FOR GENERATING ANTIBODIES

(75) Inventors: Giulio F. Paciotti, Columbia, MD (US); Ramadevi Raghunandan, Rockville, MD (US); Marja S. Huhta, Seattle, WA (US); Lawrence Tamarkin, Rockville, MD (US)

(73) Assignee: CytImmune Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/106,745

(22) Filed: May 12, 2011

(65) Prior Publication Data

US 2011/0275123 A1  Nov. 10, 2011

Related U.S. Application Data

(63) Continuation of application No. 12/267,847, filed on Nov. 10, 2008, now Pat. No. 7,960,145.

(60) Provisional application No. 60/986,494, filed on Nov. 8, 2007, provisional application No. 61/124,079, filed on Apr. 11, 2008.

(51) Int. Cl.
*C07K 16/12* (2006.01)
*C07K 16/22* (2006.01)
*C07K 16/24* (2006.01)
*C07K 16/28* (2006.01)
*C07K 16/30* (2006.01)
*C12N 5/02* (2006.01)
*C12N 5/07* (2010.01)
*C12P 21/00* (2006.01)
*C12P 21/08* (2006.01)

(52) U.S. Cl.
USPC ....... 435/70.21; 435/71.1; 435/325; 435/326; 435/347; 435/373; 530/387.3; 530/388.1; 536/23.5

(58) Field of Classification Search
None
See application file for complete search history.

(56) References Cited

U.S. PATENT DOCUMENTS

| | | | |
|---|---|---|---|
| 2,768,958 A | 10/1956 | Stewart et al. |
| 2,785,153 A | 3/1957 | Locke et al. |
| 3,145,144 A | 8/1964 | Ando et al. |
| 3,149,036 A | 9/1964 | Woodhour et al. |
| 3,269,912 A | 8/1966 | Grafe |
| 3,399,263 A | 8/1968 | Strazdins et al. |
| 3,531,565 A | 9/1970 | Webb et al. |
| 3,577,523 A | 5/1971 | Stolar et al. |
| 3,651,211 A | 3/1972 | Gillchriest et al. |
| 3,819,820 A | 6/1974 | Lorina et al. |
| 3,919,413 A | 11/1975 | Mebus |
| 3,983,228 A | 9/1976 | Woodhour et al. |
| 4,016,252 A | 4/1977 | Relyveld |
| 4,053,587 A | 10/1977 | Davidson et al. |
| 4,069,313 A | 1/1978 | Woodhour et al. |
| 4,177,263 A | 12/1979 | Rosenberg et al. |
| 4,196,185 A | 4/1980 | Focella et al. |
| 4,197,237 A | 4/1980 | Leute et al. |
| 4,197,286 A | 4/1980 | Rao |
| 4,213,964 A | 7/1980 | Buckler |
| 4,215,036 A | 7/1980 | Malley |
| 4,218,436 A | 8/1980 | Fitzpatrick |
| 4,329,281 A | 5/1982 | Christenson et al. |
| 4,330,530 A | 5/1982 | Baker |
| 4,332,787 A | 6/1982 | Homcy et al. |
| 4,339,437 A | 7/1982 | Rosenberg et al. |
| 4,346,074 A | 8/1982 | Gilmour et al. |
| 4,451,570 A | 5/1984 | Royston et al. |
| 4,487,780 A | 12/1984 | Scheinberg |
| 4,578,270 A | 3/1986 | Csizer et al. |
| 4,594,325 A | 6/1986 | Lundak |
| 4,608,252 A | 8/1986 | Khanna et al. |
| 4,624,921 A | 11/1986 | Larrick et al. |
| 4,624,923 A | 11/1986 | Margel |
| 4,639,336 A | 1/1987 | Jouquey et al. |
| 4,657,763 A | 4/1987 | Finkelstein |
| 4,693,975 A | 9/1987 | Kozbor et al. |
| 4,710,378 A | 12/1987 | Ohtomo et al. |
| 4,720,459 A | 1/1988 | Winkelhake |

(Continued)

FOREIGN PATENT DOCUMENTS

| | | |
|---|---|---|
| AU | 760035 | 8/2003 |
| AU | 757357 | 3/2004 |

(Continued)

OTHER PUBLICATIONS

Author: Title: PCT International Search Report PCT/US04/40785 Publ: *PCT International Search Report* vol. /Iss: pp. 1-2 Date: Oct. 25, 2005.
Author: Title: EPO Supplementary Search Report—04821049.6 Publ: *EPO Search Report* vol. /Iss: pp. 1-11 Date Oct. 19, 2009.
Author: Title: Australian Office Action—Application No. 2004311630 Publ: *Australian Office Action* vol. /Iss: pp. 1-4 Date: Oct. 9, 2009.
Author: Title: Office Action—Peoples Republic of China—Application No. 200480041234.5 Publ: *Peoples Republic of China—Office Action* vol. /Iss: pp. 1-18 Date: Jun. 27, 2008.
Author: Title: PCT International Search Report PCT/US08/82984 Publ: *PCT International Search Report* vol. /Iss: pp. 1-4 Date: Feb. 3, 2009.

(Continued)

*Primary Examiner* — Bridget E Bunner
*Assistant Examiner* — Fozia Hamud
(74) *Attorney, Agent, or Firm* — F. Brent Nix; Johnson, Marcou & Isaacs, LLC

(57) ABSTRACT

The compositions and methods of the present invention comprise the efficient and effective presentation of antigens to the appropriate components of the immune system resulting in the production of species-specific antibodies in vitro. In general, these compositions comprise one or more antigenic components together with a colloidal metal, optionally combined with derivatized PEG (polyethylene glycol) or other agents. The invention also comprises methods and compositions for making such colloidal metal compositions.

29 Claims, 24 Drawing Sheets

U.S. PATENT DOCUMENTS

| | | | |
|---|---|---|---|
| 4,740,589 A | 4/1988 | Moreno |
| 4,744,760 A | 5/1988 | Molday |
| 4,753,873 A | 6/1988 | Beltz et al. |
| 4,812,556 A | 3/1989 | Vahlne et al. |
| 4,880,750 A | 11/1989 | Francoeur |
| 4,882,423 A | 11/1989 | Taguchi et al. |
| 4,906,564 A | 3/1990 | Lyon et al. |
| 4,977,286 A | 12/1990 | Nicolaou et al. |
| 5,017,687 A | 5/1991 | Vahlne et al. |
| 5,019,497 A | 5/1991 | Olsson |
| 5,035,995 A | 7/1991 | Taguchi et al. |
| 5,112,606 A | 5/1992 | Shiosaka et al. |
| 5,126,253 A | 6/1992 | Nakanishi et al. |
| 5,169,754 A | 12/1992 | Siiman et al. |
| 5,242,828 A | 9/1993 | Bergstrom et al. |
| 5,248,772 A | 9/1993 | Siiman et al. |
| 5,264,221 A | 11/1993 | Tagawa et al. |
| 5,294,369 A | 3/1994 | Shigekawa et al. |
| 5,376,556 A | 12/1994 | Tarcha et al. |
| 5,384,073 A | 1/1995 | Shigekawa et al. |
| 5,434,088 A | 7/1995 | Ikeda et al. |
| 5,436,161 A | 7/1995 | Bergstrom et al. |
| 5,446,090 A | 8/1995 | Harris |
| 5,466,609 A | 11/1995 | Siiman et al. |
| 5,498,421 A | 3/1996 | Grinstaff et al. |
| 5,521,289 A | 5/1996 | Hainfeld et al. |
| 5,639,725 A | 6/1997 | O'Reilly et al. |
| 5,686,578 A | 11/1997 | Goldenberg |
| 5,972,720 A | 10/1999 | Nichtl et al. |
| 6,274,552 B1 | 8/2001 | Tamarkin et al. |
| 6,407,218 B1 * | 6/2002 | Tamarkin et al. ......... 530/389.1 |
| 6,447,765 B1 | 9/2002 | Horwitz |
| 6,528,051 B2 | 3/2003 | Tamarkin et al. |
| 6,528,485 B1 | 3/2003 | Veronese et al. |
| 6,530,944 B2 | 3/2003 | West et al. |
| 6,624,886 B2 | 9/2003 | Natan et al. |
| 6,734,168 B2 | 5/2004 | Stern et al. |
| 6,869,932 B2 | 3/2005 | Veronese et al. |
| 7,229,841 B2 | 6/2007 | Tamarkin et al. |
| 7,387,900 B2 | 6/2008 | Tamarkin et al. |
| 7,547,438 B2 | 6/2009 | Thomas et al. |
| 7,960,145 B2 * | 6/2011 | Paciotti et al. ......... 435/70.21 |
| 2001/0055581 A1 | 12/2001 | Tamarkin et al. |
| 2003/0053983 A1 | 3/2003 | Tamarkin et al. |
| 2003/0180252 A1 | 9/2003 | Tamarkin et al. |
| 2004/0018203 A1 | 1/2004 | Pastan et al. |
| 2004/0029794 A1 | 2/2004 | Veronese et al. |
| 2004/0054139 A1 | 3/2004 | Page et al. |
| 2004/0204576 A1 | 10/2004 | Jackson et al. |
| 2004/0213760 A1 | 10/2004 | Tamarkin et al. |
| 2005/0003431 A1 | 1/2005 | Wucherpfennig et al. |
| 2005/0175583 A1 | 8/2005 | Tamarkin et al. |
| 2005/0175584 A1 | 8/2005 | Paciotti et al. |
| 2006/0222595 A1 | 10/2006 | Mukherjee et al. |
| 2006/0280738 A1 | 12/2006 | Tedder |
| 2007/0014798 A1 | 1/2007 | Rieber |
| 2007/0160572 A1 | 7/2007 | Tamarkin et al. |
| 2007/0231408 A1 | 10/2007 | Tamarkin et al. |

FOREIGN PATENT DOCUMENTS

| | | |
|---|---|---|
| AU | 2003204353 | 11/2006 |
| CA | 2158475 | 3/1994 |
| EP | 0 044 722 | 1/1982 |
| EP | 0 156 242 | 12/1985 |
| EP | 0 179 483 | 4/1986 |
| EP | 0 269 408 | 6/1988 |
| EP | 0 441 120 A2 | 8/1991 |
| EP | 0 489 465 A2 | 6/1992 |
| EP | 0 667 398 A2 | 8/1995 |
| EP | 0 811 846 B1 | 12/1997 |
| EP | 0 486 526 B2 | 3/2001 |
| EP | 1 401 376 | 3/2004 |
| EP | 1 039 933 B1 | 2/2006 |
| FR | 2 334 366 | 7/1977 |
| FR | 2 533 827 | 4/1984 |
| GB | 981242 | 1/1965 |
| JP | 05-017369 | 1/1993 |
| JP | 6-118083 | 4/1994 |
| WO | WO 90/05303 A1 | 5/1990 |
| WO | WO 91/02078 A1 | 2/1991 |
| WO | WO 91/15242 A1 | 10/1991 |
| WO | WO 93/21528 A1 | 10/1993 |
| WO | WO 94/21240 A2 | 9/1994 |
| WO | WO 94/21288 | 9/1994 |
| WO | WO 96/04313 | 2/1996 |
| WO | WO 97/29131 A1 | 8/1997 |
| WO | WO 99/24066 | 5/1999 |
| WO | WO 99/24077 A2 | 5/1999 |
| WO | WO 02/087509 A2 | 11/2002 |
| WO | WO 2005/065121 A3 | 7/2005 |
| WO | WO 2005/072893 A1 | 8/2005 |

OTHER PUBLICATIONS

Author: Bae et al. Title: Thermo-Sensitive Pluronic Micelles Stabilized by Shell Crossing-Linking with Gold Nanoparticles Publ: Vol. / Iss: pp. 1-4 Date: Mar. 10, 2006.

Author: Balkwill et al. Title: The Cytokine Network Publ: *Immunology Today* vol. /Iss: 10 (9) pp. 299-304 Date: Jan. 1, 1989.

Author: Borrebaeck et al. Title: Human Monoclonal Antibodies Produced by Primary in Vitro Immunization of Peripheral Blood Lymphocytes *Proceedings of the National Academy of Science USA* vol. /Iss:85 pp. 3995-3999 Date: Jun. 1, 1988.

Author: Brust et al. Title: Novel Gold-Dithiol Publ: Nano-Networks with Non-Metallic Electronic Properties Publ: *Advanced Materials* vol. /Iss:7 (9) pp. 795-797 Date: Jan. 1, 1995.

Author: Calabresi et al. Title: Chemotherapy of Neoplastic Disease Publ: *Goodman & Gilman's The Pharmacological Basis of Therapeutics* vol. /Iss:9th Edition pp. 1225-1232 Date: Jan. 1, 1996.

Author: Ciesiolka et al. Title: An 8- to 10-fold Enhancement in Sensitivity for Quanitation of Proteins by Modified Application of Colloidal Gold Publ: *Analytical Biochemistry* vol. /Iss:168 (2) pp. 280-283 Date: Feb. 1, 1988.

Author: Coulombe et al. Title: Cytochemical Demonstration of Increased Phospholipid Content in Cell Membranes in Chlorphentermine-Induced Phospholipidosis Publ: *Journal of Histochemistry and Cytochemistry* vol. /Iss:37 (2) pp. 139-147 Date: Jan. 1, 1989.

Author: De Brabander et al. Title: Probing Microtubule-Dependent Intracellular Motility with Nanometre Particle Video Ultramicroscopy (nanovid ultramicroscopy) (Abstract Only—Applicants do not have complete copy) Publ: *Cytobios* vol. /Iss:43 pp. 273-283 Date: Jan. 1, 1985.

Author: Deng et al. Title: Self-Assembled Monolayers of Alkanethiolates Presenting Tri(propylene sulfoxide) Groups Resist the Adsorption of Protein Publ: *Journal of the American Chemical Society* vol. /Iss:118 (19) pp. 5136-5137 Date: May 15, 1996.

Author: Dominguez et al. Title: Effect of Heat Treatment on the Antigen-Binding Activity of Anti-Peroxidase Immunoglobulins in Bovine Colostrum Publ: *Journal of Dairy Science* vol. /Iss:80 (12) pp. 3182-3187 Date: Dec. 1, 1998.

Author: Elliot et al. Title: Analysis of Colloidal Gold Probes by Isoelectric Focusing in Agarose Gels Publ: *Analytical Biochemistry* vol. /Iss:186 (1) pp. 53-59 Date: Apr. 1, 1990.

Author: EPO Search Report Title: EPO Application 04821049.6 Search Report Publ: *EPO Search Report* vol. /Iss: pp. 1-10 Date: Oct. 19, 2009.

Author: EPO Searching Authority Title: Search Report EPO—Application No. 02729092.3 Publ: *EPO Search Report* vol. /Iss: pp. 1-6 Date: Jul. 13, 2009.

Author: Fraker et al. Title: Passive Immunization Against Tumor Necrosis Factor Partially Abrogates Interleukin 2 Toxicity Publ: *The Journal of Experimental Medicine* vol. Iss: 170 pp. 1015-1020 Date: Jan. 1, 1989.

Author: Gallergo et al. Title: Ultrastructural Identification of the Splenic Follicular Dendritic Cells in the Chicken Publ: *The Anatomical Record* vol. /Iss:242 pp. 220-224 Date: Jan. 1, 1995.

Author: Goldstein et al. Tilte: Cardiovascular Effects of Platelet-Activating Factor Publ: *Lipids* vol. /Iss:26 (212) pp. 1250-1256 Date: Jan. 1, 1991.

Author: Grainger et al. Title: Polymeric Monolayers on Solid Substrates by Spontaneous Adsorption from Solution Publ: *American Chemical Society—Abstracts of papers* vol. /Iss:Part 1 pp. Paragraph 074 Date: Aug. 20, 1995.
Author: Gref et al. Title: The Controlled Intravenous Delivery of Drugs using PEG-Coated Sterically Nanospheres Publ: *Advanced Drug Delivery Reviews* vol. /Iss: 16 pp. 215-233 Date: Jan. 1, 1995.
Author: Title: USPTO Office Action Action U.S. Appl. No. 12/267,847 Publ: U.S. PTO Office Action vol. /Iss: pp. 1-11 Date: Oct. 5, 2010.
Author: Title: USPTO Office Action U.S. Appl. No. 12/267,847 Publ: USPTO Office Action vol. /Iss: pp. 1-11 Date: Mar. 18, 2010.
Author: Hashimoto et al. Title: Action Site of Circulating Interleukin-1 on the Rabbit Brain Publ: *Brain Research* vol. /Iss:540 pp. 217-223 Date: Jan. 1, 1991.
Publ: Hisamatsu et al. Title: Platelet Activating Factor Induced Respiratory Mucosal Damage Publ: *Lipids* vol. /Iss:26 (12) pp. 1287-1291 Date: Jan. 1, 1991.
Author: Hopkins et al. Title: Early Events Following the Binding of Epidermal Growth Factor to Surface Receptors on Ovarian Granulosa Cells Publ: *European Journal of Cell Biology* vol. /Iss:24 pp. 259-264 Date; Jan. 1, 1981.
Author: Ishii et al. Title: Preparation of Functionally PEGylated Gold Nanoparticles with Narrow Distribution through Autoreduction of Auric Cation by a-Biotinyl-PEG-block-[poly(2-N,N-dimethylamineo)ethyl methyacrylate)] Publ: *Langmuir* vol. /Iss:20 pp. 561-564 Date: Feb. 3, 2004.
Author: Ito et al. Title: Antitumor Reactivity of Anti-CD3/Anti-CD28 Bead-Activated Lymphoid Cells: Implications for Cell Therapy in a Murine Model Publ: *Journal of Immunotherapy* vol. Iss:26 (3) pp. 222-233 Date: Jan. 1, 2003.
Author: Japanese Patent Office Title: Japanese Patent Application 2000-520153 Office Action as translated by Foreign Associate Publ: *Japanese Office Action* vol. /Iss: pp. 1-10 Date: Oct. 6, 2009.
Author: Japanese Publication Title: Japanese Laid-Open Publication No. 9-107980 English Abstract only—of Japanese Publ: Patent Application 08-231415 vol. /Iss: pp. 1-3 Date: Apr. 28, 1997.
Author: Title: USPTO Office Action—U.S. Appl. No. 11/004,623 Publ: USPTO Office Action vol. /Iss: pp. 1-16 Date: Nov. 6, 2007.
Author: Title: USPTO Office Action—U.S. Appl. No. 12/549,207 Publ: USPTO Office Action vol. /Iss: pp. 1-8 Date: Aug. 17, 2010.
Author: Title: USPTO Office Action—U.S. Appl. No. 11/004,623 Publ: USPTO Office Action vol. /Iss: pp. 1-12 Date: Aug. 5, 2008.
Author: Juedes, Amy E.—USPTO Title: USPTO Office Action—U. S. Appl. No. 11/004,623 Publ: USPTO Office Action vol. /Iss: pp. 1-22 Date: Feb. 22, 2007.
Author: Kang et al. Title: Ultrastructural Immunocytochemical Study of the Uptake and Distribution of Bacterial Lipopolysaccride in Human Monocytes Publ: *Journal of Leukoycte Biology* vol. /Iss:48 pp. 316-332 Date: Jan. 1, 1990.
Author: Kimball Title: Chapter 7—B Lymphocytes Publ: *Introduction to Immunology* vol. /Iss: pp. 184-190 Date: Jan. 1, 1990.
Author: Kirchner et al. Title: The Development of Neutralizing Antibodies in a Patient Receiving Subcutaneous Recombinant and Natural Interleukin-2 Publ: *Cancer* vol. /Iss:67 (7) pp. 1862-1864 Date: Apr. 1, 1991.
Author: Koganty, R.R. Title: Vaccine Safety: A Case for Synthetic Vaccine Formulations Publ: *Expert Review of Vaccines* vol. /Iss:2 (6) pp. 725-727 Date: Dec. 1, 2003.
Author: Koning, et al. Title: Selective Transfer of a Lipophilic Prodrug of 5-Fluorodeoxyuridine from Immunoliposomes to Colon Cancer Cells Publ: *Biochimica et Biphysica Acta* vol. /Iss:1420 pp. 153-167 Date: Jun. 2, 1999.
Author: Lang et al. Title: A New Class of Thiolipids for the Attachment of Lipid Bilayers on Gold Surfaces Publ: *Langmuir* vol. /Iss:10 (1) pp. 197-210 Date: Jan. 1, 1994.
Author: Lanzavecchia Title: Identifying Strategies for Immune Interventor Publ: *Science* vol. /Iss:260 pp. 937-944 Date: Jan. 1, 1993.
Author:Lemmon et al. Title: Preparation and Characterization of Nanocomposites of Poly(ethylene oxide) with Layered Solids Publ: *New Techniques and Approaches* vol. /Iss:Chapter 5 pp. 43-54 Date: Jan. 1, 1995.

Author:Leuvering et al. Title: A Sol Particle Agglutination Assay for Human Chorionic Gonadotrophin Publ: *Journal of Immunological Methods* vol. /Iss:45 (2) pp. 183-194 Date: Jan. 1, 1981.
Author:Lezzi et al. Title: Chelating Resins Supporting Dithiocarbamate and Methylthiourea Groups in Adsorption of Heavy Metal Ions Publ: *Journal of Applied Polymer Science* vol. /Iss:54(7) pp. 889-897 Date: Nov. 14, 1994.
Author: Lezzi et al. Title: Synthesis of Thiol Chelating Resins and Their Adsorption Properties toward Heavy Metal Ions Publ: *Journal of Polymer Science* vol. /Iss:32 pp. 1877-1883 Date: Jan. 1, 1994.
Author: Li et al. Title: Self-Assembled Multilayes of Alternating Gold Nanoparticles and Dithols: Approaching to Superlattice Publ: *Colloids and Surface A* vol. /Iss:175 pp. 217-223 Date: Jan. 1, 2000.
Author:Li et al. Title: Plasma Protein Interactions with Copolymer-Stabilized Colloids Publ: *Dissertation Abstract International* vol. /Iss:54(7) pp. 3735-B Date: Jan. 1, 1994.
Author: Magez et al. Title: Spectic Uptake of Tumor Necrosis Factor is Involved in Growth Control of *Trypanosoma brucei* Publ: *The Journal of Cell Biology* vol. /Iss:137 (3) pp. 715-727 Date: May 5, 1997.
Author: Mantis, N. J. Title: Vaccines Against Category B Toxins? *Staphylococcal* Enterotoxin B, Epsilon Toxin and Ricin Publ: *Advanced Drug Delivery Reviews* vol. /Iss:57 pp. 1424-1439 Date: Jun. 17, 2005.
Author: Mathias et al. Title: Sulfur-Substituted Polyoxyethylenes Sequential Ether-Thioether Copolymers Publ: *Crown Ethers and Phase Transfer Catalysis in Polymer Science* vol. /Iss: pp. 359-370 Date: Jan. 1, 1984.
Author: Morris et al. Title: Validation of the Biotinyl Ligand-Avidin-Gold Technique Publ: *Cytochemistryvol* vol. /Iss:40 pp. 711-721 Date: Jan. 1, 1992.
Author: Mrksich et al. Title: Surface Plasmon Resonance Permits in Situ Measurement of Protein Adsorption on Self-Assembled Monolayers of Alkanethiolates on Gold Publ: *Langmuir* vol. /Iss:11 pp. 4383-4385 Date: Jan. 1, 1995.
Author: Nakashima et al. Title: Electrochemical Characterization of an Assembled Monolayer of -Methoxy-mercapto-poly(ethylene glycol) on Gold and Complex Formation of the Monolayer with -Cyclodextrin Publ: *Chemistry Letters* vol. /Iss: pp. 731-732 Date: Jan. 1, 1996.
Author: Niwa et al. Title: Two-Dimensional Array of Poly(methacrylic acid) Brushes on Gold Substrates. Interaction with Ferrocen-Terminated Poly(oxyethylene)s Publ: *Macromolecules* vol. /Iss:28 (23) pp. 7770-7774 Date: Nov. 6, 1995.
Author: Ohmann et al. Title: Expression of Tumor Necrosis Factor-Receptors on Bovine Macrophges, Lymphocytes and Polymorphonuclear Luekocytes, Internalization of Receptor-Bound Ligand, and Some Functional Effects Publ: *Lymphokine Research* vol. /Iss:9 (1) pp. 43-58 Date: Jan. 1, 1990.
Author: Otsuka et al. Title: Quantitative and Reversible Lectin-Induced Association of Gold Nanoparticles Modified with -Lactosyl-mercapto-poly(ethylene glycol) Publ: *Journal of the American Chemical Society* vol. /Iss: 123 pp. 8226-8230 Date: Feb. 20, 2001.
Author: Paciotti et al. Title: Colloidal Gold: A Novel Nanoparticle Vector for Tumor Directed Drug Delivery Publ: *Drug Delivery* vol. /Iss:11 (3) pp. 169-183 Date: May 1, 2004.
Author: Paciotti et al. Title: (XP-001537146) #3858—Comparison of the Toxicity and Pharmacokinetics of Neat and Colloidal Gold Bound TNF Publ: *Proceedings of the American Association for Cancer Research* vol. /Iss:40 pp. 585 Date: Mar. 1, 1999.
Author: Paciotti et al. Title: (XP-001537149) #104—The Use of Colloidal Gold in Cytokine Immununotherapy Publ: *Proceedings of the American Association for Cancer Research* vol. /Iss:39 pp. 153 Date: Mar. 1, 1998.
Author: Paciotti et al. Title: Interleukin 1 Differentially Synchronizes Estrogen Dependent and Estrogen-Independent Human Breast Cells in $G_0/G_1$ Phase of the Cell Cycle Publ: *Anti-Cancer Research* vol. /Iss: 11 pp. 25-32 Date: Jan. 1, 1991.
Author: Paciotti et al. Title: Interleukin 2 Differentially Effects the Proliferatino of a Hormone-Dependent and a Hormone-Independent Human Breast Cancer Cell Line in Vitro and in Vivo Publ: *Anti-Cancer Research* vol. /Iss: 8 pp. 1233-1240 Date: Jan. 1, 1988.

Author: Paciotti et al. Title: Interleukin 1 Directly Regulates Hormone-Dependent Human Breast Cancer Cell Proliferation in Vitro Publ: *Molecular Endocrinology* vol. /Iss:2 pp. 459-464 Date: Jan. 1, 1988.

Author: Peters et al. Title: Binding and Internalization of Biotinylated Interleukin-2 in Human Lymphocytes Publ: *Blood* vol. /Iss:76 pp. 97-104 Date: Jan. 1, 1990.

Author: Prakken et al. Title: Artificial Antigen-Presenting Cells as a Tool to Exploit the Immune 'Synapse' Publ: *Nature Medicine* vol. /Iss:6 (12) pp. 1406-1410 Date: Dec. 1, 2000.

Author: Prime et al. Title: Adsorption of Proteins onto Surfaces Containing End-Attached Oligo(ethylene oxide): A Model System Using Self-Assembled Monolayers Publ: *Journal of the American Chemical Society* vol. /Iss:115 pp. 10714-10721 Date: Jan. 1, 1993.

Author: Rabolt, J.F. Title: Design and Construction of Two Component Heterogenous Polymer Surfaces by Self Assembly Publ: *Polymer Preprints* vol. /Iss:36 (1) pp. 84 Date: Apr. 1, 1995.

Author: Roitt et al. Title: The Cytokine Network Publ: *Immunology* vol. /Iss:3rd ed. pp. 8-15 Date: Jan. 1, 1993.

Author: Stolnik et al. Title: The Effect of Surface Coverage and Conformation of Poly(ethylene oxide) (PEO) Chains of Poloxamer 407 on the Biological Fate of Model Colloidal Drug Carriers Publ: *Biochimica et Biphysica Acta* vol. /Iss:1514 pp. 261-279 Date: Oct. 1, 2001.

Author: Thompson et al. Title: A Phase I Trial of CD3/CD28 -Activated T Cells (Xcellerated T Cells) and Interleukin-2 in Patients with Metastatic Renal Cell Carcinoma Publ: *Clinical Cancer Research* vol. /Iss:9 pp. 3562-3570 Date: Sep. 1, 2003.

Author: Tomii et al. Title: Production of Anti-Platelet-Activating Factor Antibodies by the Use of Colloidal Gold as Carrier (Japanese Article—English translation provided) Publ: *Japanese Journal of Medical Science and Biology* vol. /Iss:44 pp. 75-80 Date: Jan. 1, 1991.

Author: Title: USPTO Office Action—U.S. Appl. No. 11/046,204 Publ: USPTO Office Action vol. /Iss: pp. 1-20 Date: Oct. 16, 2008.

Author: Title: USPTO Office Action—U.S. Appl. No. 11/516,175 Publ: USPTO Office Action vol. /Iss: pp. 1-9 Date: Jun. 5, 2009.

Author: Van Rensen et al. Title: Liposomes with Incorporated MHC Class II/Peptide Complexes as Antigen Presenting Vesicles for Specific T Cell Activation Publ: *Pharmaceutical Research* vol. /Iss:16 (2) pp. 198-204 Date: Jan. 1, 1999.

Author: Vidal et al. Title: Steric Stabilization of Polystyrene Colloids Using Thiol-ended Polyethylene Oxide Publ: *Polymers for Advanced Technologies* vol. /Iss:6 pp. 473-479 Date: Nov. 15, 1994.

Author: Walden et al. Title: Induction of Regulatory T-lymphocyte Responses by Liposomes Carrying Major Histocompatibility Complex Molecules and Foreign Antigen Publ: *Nature* vol. /Iss:315 pp. 327-329 Date: May 23, 1985.

Author: Title: Clinical & Diagnostic Applications—Dynabeads for Immunoassay IVD Publ: Invitrogen.com vol. /Iss: pp. 1-3 Date: Jan. 1, 2010.

Author: Weikl, M. Title: Extended EPO Search Report—Application No. EP 08847122.2 Publ: vol. /Iss: pp. 1-11 Date: Oct. 24, 2011.

Author: Weikl, M. Title: Office Action issued in EPO Appl. No. 08847122.2 Publ: vol. /Iss: pp. 1-7 Date: Feb. 7, 2013.

* cited by examiner

Untreated HS-27 Cells

Toxin A  Δ-Toxin A

Toxin B  Δ-Toxin B

Fig. 2A

Table I. Denaturation of IL-2 or IL-4 on Colloidal Gold Nanoparticles
Recovery of IL-2 or IL-4 on Colloidal Gold Nanoparticles

|                      | Amount Detected (µg/ml) | |
|----------------------|-------|-------|
| Amount Added (µg/ml) | IL-2  | IL-4  |
| 1.57                 | 0.01  | 0.12  |
| 3.15                 | 0.3   | 0.34  |
| 6.3                  | 0.3   | 0.4   |

TABLE II

| Cytokine Concentration (pg/ml) | Immunizing Antigen | | |
|---|---|---|---|
| | Unstimulated | Native TNF | ΔTNF |
| *IL-2* | *3.5* | *506* | *3194* |
| IL-3 | 2.2 | 2.6 | 10.9 |
| IL-4 | 1.6 | 14.9 | 5.61 |
| IL-5 | 18.1 | 347 | 397 |
| *IL-6* | *16.9* | *58.2* | *211* |
| IL-7 | 0.5 | 1.2 | 1.1 |
| IL-8 | 16.9 | 2430 | 3122 |
| IL-9 | 24.1 | 25.7 | 21.4 |
| *IL-10* | *1.3* | *41.5* | *656* |
| IL-12 | 5 | 40 | 30 |
| *IL-13* | *21.2* | *4227* | *13360* |
| *CD40-L* | *1.3* | *3220* | *12378* |
| *GMCSF* | *206* | *297* | *3197* |
| ICAM-1 | 9.9 | 17790 | 15000 |
| Cytokine Receptor Concentration (pg/ml) | | | |
| IL-6 R | 1.4 | 942 | 266 |
| IL-12 R | 1.6 | 7691 | 14553 |
| TNFR1 | 4.4 | 1096 | 651 |
| TNFR2 | .5 | 1209 | 1546 |

Fig. 5B

COMPOSITIONS AND METHODS FOR GENERATING ANTIBODIES

CROSS REFERENCE TO RELATED PATENT APPLICATIONS

This application is a continuation of U.S. patent application Ser. No. 12/267,847, filed Nov. 10, 2008, now U.S. Pat. No. 7,960,145, which claims the benefit of U.S. Provisional Patent Application No. 60/986,494, filed Nov. 8, 2007, and U.S. Provisional Patent Application No. 61/124,079, filed Apr. 11, 2008.

FIELD OF THE INVENTION

The present invention relates to novel compositions and methods for antigen presentation. More specifically, the present invention relates to the presentation and delivery of antigens and other agents to human and animal cells for eliciting a desired immune response. The compositions and methods of the present invention involve the use of colloidal metals for making and using such compositions. In addition, the present invention relates to novel in vitro culture systems for producing antibodies.

BACKGROUND OF THE INVENTION

In 1975 Kohler and Milstein reported the generation of the first monoclonal antibody. Their landmark paper describes the methods for fusing antibody-producing B cells, isolated from the spleens of immunized mice, with aggressively proliferating mouse myeloma cells. This resultant hybrid cell, a so-called hybridoma, possesses the characteristics of both parental cells; it produces and secretes large amounts of antibody during its continued growth and proliferation. Through a series of systematic cellular dilutions, genetically singular hybridoma cells are isolated that produce an antibody of singular isotype specificity, a so-called monoclonal antibody (mAb).

Due to their exquisite specificity, mAbs held the promise for developing "magic bullet" therapies for treating human disease. Nevertheless, over the past 40 years a mere handful of human mAbs have been developed into therapeutics. To understand the reason for this apparent failure, one must appreciate the events occurring during the in vivo antibody response, and how past attempts to replicate them for developing human mAbs were unsuccessful.

The most common procedure for generating monoclonal antibodies starts with the immunization of an animal with the antigen of interest. The antigen, draining into a local lymph node or spleen, activates naïve B cells to proliferate and produce IgM antibodies against the antigen. These activated B cells are then instructed by antigen-activated CD4$^+$ T-cells to undergo a process known as class switching. During class switching, the B cell immunoglobulin gene is reorganized, resulting in a switch in the type of antibody produced from low-affinity IgMs to high affinity IgGs.

As the antibody response progresses, the progeny of the original parental B cells continue to proliferate in the lymph node and spleen to give rise to a structure known as the germinal center. Within the germinal center, proliferating B cells are exposed to additional cellular and chemical signals that induce the Bcells to undergo somatic hypermutation and affinity maturation. During somatic hypermutation, point mutations are introduced into the immunoglobulin variable region gene sequences that alter the antibody's affinity for binding the antigen. During affinity maturation, B cells expressing antibodies with higher antigen affinities continue to proliferate and are signaled to differentiate into either plasma cells or memory B cells. B cells possessing deleterious mutations are deleted by apoptosis. Typically, at this stage of mAb development, B cells are isolated from the lymph node or spleen of the immunized animal, and are fused with species-specific myeloma cells. The fused cells are allowed to grow to produce antigen specific IgG antibodies, which are screened for potential use in human therapeutics.

The early success of this technology in animals prompted scientists in the 1980's to extend this concept for the production of human mAbs. However, extrapolation from animal to man was fraught with difficulties. The first hurdle investigators faced was the lack of antigen specific B cells. Recall that under standard procedures, antigen specific B cells are typically harvested from immunized animals; a method not generally applicable to humans unless the long-term safety of the antigen used for immunization is known. This problem is further compounded by (i) the fact that there is no ready source of activated B cells, and (ii) the inability to obtain either lymph nodes or spleens from human subjects. These factors prompted the development of a variety in vitro strategies to produce human monoclonal antibodies.

Although initial results showed great promise, the inability of past technologies to completely reconstruct the sequence of events of the in vivo antibody response ultimately caused them to fail. To date three technologies have been developed to address these challenges and are currently used for the development of human monoclonal antibody therapeutics.

The oldest of these technologies is the humanization of murine monoclonal antibodies to form a human mouse chimeric (i.e., humanized) antibody. Using this technology, murine monoclonal antibodies to a putative human antigen are generated in the traditional methods of Kohler and Milstein. Nevertheless, such antibodies have little to no utility as human therapeutics since they are generated in mice and thus would elicit a human anti mouse antibody response (HAMA response) in humans. To reduce the immunogenicity of the murine monoclonal antibody the FAb (fraction antigen binding) fragment of the murine mAb was chemically weaved into the structure of a human antibody molecule. Although these humanized antibodies were less immunogenic in people, the murine segments still posed a challenge due to their residual immunogenicity.

A second technology, Phage Display, uses vast phage libraries expressing random sequences of the human antibody variable region. These libraries are screened to select specific vectors that will bind a putative human antigen target. Once identified the specific bacteriophage are grown and then processed to collect the FAb domain. Although this technology generates antibodies that are fully human, the process requires library screening and multiple cloning steps to achieve a fully human antibody.

The transgenic mouse represents the final technology that is currently used to generate fully human antibodies. Simply put, these mice have been genetically engineered to contain the fully human equivalent of the genes that control the murine immune response. This technology seems to address all of the prior pitfalls of human mAb development since the putative therapeutic is of fully human origins and thus should not elicit an antibody response. Nevertheless, although the transgenic mouse technology has existed since 1993, fully human monoclonal antibodies generated are not commonplace.

What is needed therefore, are effective compositions and methods for the generation of antibodies. More specifically, what is needed are compositions and methods for the generation of species specific antibodies (for example, fully human antibodies against human target antigens). Such methods should comprise the efficient and effective presentation of antigens to the appropriate components of the immune systems. Preferably, such methods should be species specific, promoting for example, the generation of human antibodies for use in humans without eliciting undesired immunogenic reactions. What is also needed are methodologies that do not cause unwanted side effects in the entire organism. In addition what is needed are methods for generating human anti-human monoclonal antibodies from peripheral human blood lymphocytes wherein such antibodies not only bind the human antigen, but also have been shown to neutralize the biologic action of the putative antigen.

SUMMARY OF THE INVENTION

The present invention comprises compositions and methods for the generation of desired antibodies in vitro, such as fully human antibodies, using modified or denatured antigens. The compositions and methods of the present invention comprise the efficient and effective presentation of antigens to the appropriate components of immune systems. The methods described herein are species-specific, promoting for example, the generation of human antibodies for use in humans without eliciting undesired immunogenic reactions. The methodologies of the present invention do not cause unwanted side effects in the entire organism. In addition the methods and compositions of the present invention comprise generating, in vitro, human anti-human monoclonal antibodies from immunologically relevant cells, such as peripheral human blood lymphocytes, wherein such antibodies not only bind the human antigen, but also to neutralize the biologic action of the putative antigen.

The present invention comprises compositions and methods for presentation of antigens, nucleic acid sequences and any other biological factors capable of eliciting an immune response. In general, the compositions of the present invention comprise antigen formulations optionally comprising one or more antigens together with a colloidal metal. In the method of the present invention, the antigen may be modified or denatured, and in certain embodiments the antigen may be bound to a colloidal metal such as colloidal gold. In addition, the present invention provides unique culture systems that enable the customized production of antibodies. The culture systems are flexible and amenable to various factors resulting in the production of antibodies having specificity for particular antigen(s) and belonging to a desired immunoglobulin class (for example, IgG, IgA, etc.).

The compositions and methods of the present invention are particularly useful in eliciting desired immune responses. In particular, the compositions and methods of the present invention are useful for stimulating the production of species-specific antibodies. For example, in contrast to currently available methodologies wherein elicited antibodies frequently include a murine response, the current methods are specific for the intended recipient, including but not limited to, animals such as humans, cows, chickens, horses, chimpanzees, and birds.

The present invention overcomes the problem of the prior art associated with the modification of the antigen. It is generally accepted that immunological use of modified or denatured antigens is T cell rather than B cell stimulatory. However, the present invention describes a methodology for overcoming this challenge, and teaches how antigens may be modified and manipulated to generate a desired immunological response without T cells.

In addition, the present invention overcomes the problem of an appropriate culture system for producing desired antibodies. Until now, the use of mice or transgenic mice was the predominant method of choice for producing antibodies. These methods are limited as the resulting antibodies frequently generate an anti-mouse response in the host. The present invention provides a unique and customizable culture system enabling the production of effective and species-specific antibodies.

Accordingly, it is an object of the present invention to provide methods and compositions for generating specifically desired antibodies.

It is another object of the present invention to provide methods and compositions for manipulating and modifying antigens for generating a specifically desired immunological response.

Another object of the present invention is to provide methods and compositions for generating a specifically desired immunological response in vitro comprising the use of modified or denatured antigens optionally combined with a colloidal metal.

It is yet another object of the present invention to provide methods and compositions for generating a specifically desired immunological response in vitro comprising the use of denatured antigens in combination with a colloidal metal wherein the metal is gold.

It is yet another object of the present invention to provide methods and compositions for generating a specifically desired antibody comprising the use of denatured antigens wherein the antigen is denatured, for example, by heating or by binding to a colloidal metal.

It is yet another object of the present invention to provide methods and compositions for generating specifically desired antibodies comprising the use of a colloidal metal wherein the antigen is bound but not denatured.

Yet another object of the present invention is to provide methods and compositions for a customized culture system wherein the resultant antibody possesses desired properties.

Another object of the present invention is to provide modified or denatured antigens in an in vitro culture system that provides for antigen uptake and processing by an antigen presenting cell and B cell resulting in the generation of species-specific response such as a human anti human antibody response.

Another object of the present invention is to provide methods and compositions for generating specifically desired antibodies, comprising antibodies that recognize both the denatured and native (natural) antigen.

Yet another object of the present invention is to provide methods and compositions for generating a specifically desired immunological response comprising antibodies that recognize both denatured and native (natural) antigens wherein the antigens comprise toxins, bacteria, viruses, protozoans, nucleic acids, tumor antigens, foreign blood cells, the cells of transplanted organs or any other factors capable of eliciting an immune response.

Another object of the present invention is to provide methods and compositions for generating a specifically desired immunological response comprising antibodies that recognize both denatured and native (natural) antigens wherein the antigens comprise cytokines, and wherein the cytokines comprise lymphokines, monokines, chemokines or interleukins.

A further object of the present invention is to provide methods and compositions for generating a specifically desired immunological response comprising antibodies that recognize both denatured and native (natural) antigens wherein the antigens comprise interleukin, interferon, tumor growth factor; tumor necrosis factor.

It is yet another object of the present invention to provide methods and compositions for generating a specifically desired immunological response comprising antibodies that recognize denatured and native (natural) antigen, wherein the antigens comprise growth factors and wherein the growth factor comprises fibroblast growth factor (FGF), interleukins, kerotinocyte growth factor, colony stimulating factors, epidermal growth factor (EGF), vascular endothelial growth factor (VEGF), transforming growth factors, Schwann cell-derived growth factor, nerve growth factor (NGF), platelet-derived growth factor (PDGF), insulin-like growth factors 1 and 2 (IGF-1 and IGF-2), glial growth factor, tumor necrosis factors, prolactin and growth hormone.

It is still another object of the present invention to provide compositions for generating a specifically desired immunological response comprising antibodies that recognize both denatured and native (natural) antigen in combination with pharmaceutically acceptable adjuvants to stimulate the immune response.

Yet another object of the present invention is to provide compositions that may be administered intramuscularly, intravenously, transdermally, orally, or subcutaneously.

Another object of the present invention is to provide methods and compositions for generating a specifically desired immunological response for treating diseases in which an immune response occurs, by stimulating or suppressing components that are a part of the immune response.

Another object of the present invention is to provide methods and compositions for generating a specifically desired immunological response for therapeutic intervention in infectious disease, including but not limited to, those diseases caused by bacterial, mycological, parasitic, and viral agents.

Another object of the present invention is to provide antibodies useful for passively immunizing a human or animal.

These and other objects, features and advantages of the present invention will become apparent after a review of the following detailed description of the disclosed embodiments and the appended claims.

BRIEF DESCRIPTION OF THE DRAWINGS

FIG. 2A provides evidence showing the generation of *Clostridium Difficile* (*C. Dif*) Toxins A or B antigen by heat denaturation. Heat denaturation of the antigens was confirmed by the inability of the heated preparations to induce cell rounding as is typical for the native toxins.

FIG. 2B provides Table I showing the generation of human IL-2 and human IL-4 human antigens by binding and denaturation on colloidal gold nanoparticles. The binding of the proteins is confirmed by the ability of each protein to prevent salt-induced aggregation of the gold nanoparticles. Nevertheless, although the proteins block particle aggregation very little is detected on the particles which is indicative of protein denaturation.

FIG. 4B provides a graph of the generation of a human TNF/second (IL-2) human antigen chimera on a colloidal gold nanoparticle.

FIG. 5B provides Table II showing an example of the differential cytokine response induced by native TNF and the heat denatured TNF antigen. Given this response, it is fully anticipated that activators, such as cytokine signaling agonists or inhibitors, such as cytokine signaling antagonists or antibodies, would in turn alter the characteristics (i.e., class and subclass) of the resultant human antibody produced.

FIGS. 18A and 18B represent fully and partially neutralizing/activating human monoclonal antibodies, respectively. FIG. 18C represents a fully human monoclonal antibody that binds to the putative antigen.

DETAILED DESCRIPTION

Figure 1:
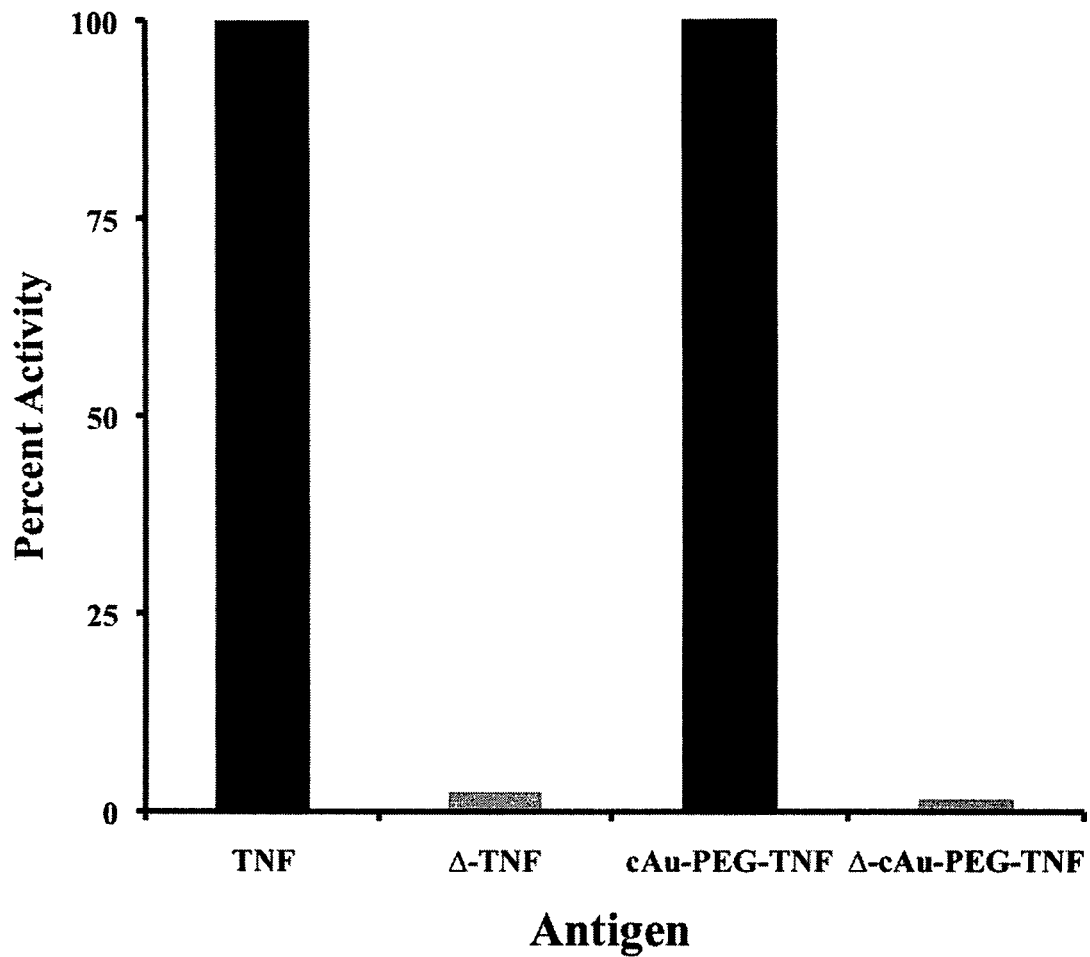
FIG. 1 provides a bar graph showing the generation of a human tumor necrosis factor alpha (TNF) antigen (soluble TNF or cAu-PEG-TNF) by heat denaturation. The heat-denatured antigens are designated by Δ (delta). % Activity is measured by ELISA and compared to the activity of the undenatured/native conformation.

The present invention may be understood more readily by reference to the following detailed description of the specific embodiments included herein. However, although the present invention has been described with reference to specific details of certain embodiments thereof, it is not intended that such details should be regarded as limitations upon the scope of the invention. The entire text of the references mentioned herein are hereby incorporated in their entireties by reference including U.S. Provisional Patent Application No. 60/986,494, filed Nov. 8, 2007, and U.S. Provisional Patent Application No. 61/124,079, filed Apr. 11, 2008.

The present invention provides compositions and methods for unique antigen presentation resulting in the in vitro generation of desired antibodies using modified or denatured antigens. The compositions and methods of the present invention comprise the efficient and effective presentation of modified or denatured antigens to the appropriate components of the immune systems in vitro. The methods described herein are species-specific, promoting for example, the generation of totally human antibodies. The present invention further provides unique culture systems that enable the production of customized antibodies. At least one novel feature of the culture systems is that controlled stimulation of the cells results in antigen specific immunoglobulin class switching.

The present invention comprises compositions and methods for the presentation and delivery of modified or denatured antigens to appropriate components of the immune system completely in vitro. In general, the present invention contemplates compositions comprising a modified or denatured antigenic component optionally combined with metal sol particles associated with any or all of the following components alone or in combinations: active agents, detection agents, targeting molecules, integrating molecules, and optionally, one or more types PEG or derivatized PEGs.

The antigen presentation methods of the present invention are used for stimulating the immune system to generate desired antibodies in an in vitro system. For example, the present invention may be used for generating fully human antibodies specific for tumor necrosis factor (TNF). Desired antibodies as achieved by the methods described herein, are useful for treatments of biological conditions, including, but not limited to, chronic and acute diseases, maintenance and control of the immune system and other biological systems, infectious diseases, vaccinations, hormonal maintenance and control, cancer, metastatic cancer, solid tumors and angiogenic states. Descriptions and uses of metal sol compositions are taught in U.S. Pat. No. 6,274,552; and related patent applications, U.S. patent application Ser. Nos. 09/808,809; 09/935,062; 09/189,748; 09/189,657, and 09/803,123; and U.S. Provisional Patent Application No. 60/287,363, all of which are herein incorporated in their entireties.

As disclosed in the Examples, the novel methods of the present invention enable the development of species-specific antibodies, such as fully human monoclonal antibodies from human precursor lymphocytes in vitro. The methods enable the generation of human anti human antibodies against various antigens including, but not limited to, recombinant human TNF alpha.

In general, the methods of the present invention use various forms of an antigen to immunize a specific species. For example, various forms of a human antigen may be used to immunize human peripheral blood lymphocytes.

The antigen may be denatured in several ways. The term "denatured" as used here in means the alteration of a protein configuration through some form of external stress (for example, by applying heat, acid or alkali, or exposure to a chaotropic agent), in such a way that it will no longer be able to carry out its cellular function. Denatured proteins can exhibit a wide range of characteristics, including partial or complete loss of activity, loss of solubility and/or aggregation. In certain embodiments, the antigen may be denatured by various means including, but not limited to, heating and/or binding to the surface of colloidal metal nanoparticles, such as colloidal gold nanoparticles. In the latter application, the mere binding of an antigen to the colloidal gold particles can cause a change in its structure so that it is no longer active or is only partially active (activity reduced). In addition to the above antigen formulations, some proteins may be antigenic as active cAu-bound complexes without needing further denaturation treatment.

In certain embodiments of the present invention, the process of generating customized species-specific antibodies comprises denaturation wherein the antigen (or antigen complex) is denatured prior to incorporation into a culture system. For example, in one embodiment, the antigen is denatured by techniques such as heat, pH, or acid/base, prior to incorporation. In another embodiment, an antigen complex may be generated by binding the antigen to a colloidal metal particle, by binding the antigen to a colloidal metal particle and then heat inactivating the complex, by binding human TNF molecules or other activators of immune response and the antigen on the same colloidal metal particle as a way of enhancing immune response, by limited heat inactivation of proteins to inactivate biological function, or by acid/base denaturation.

Figure 3A:
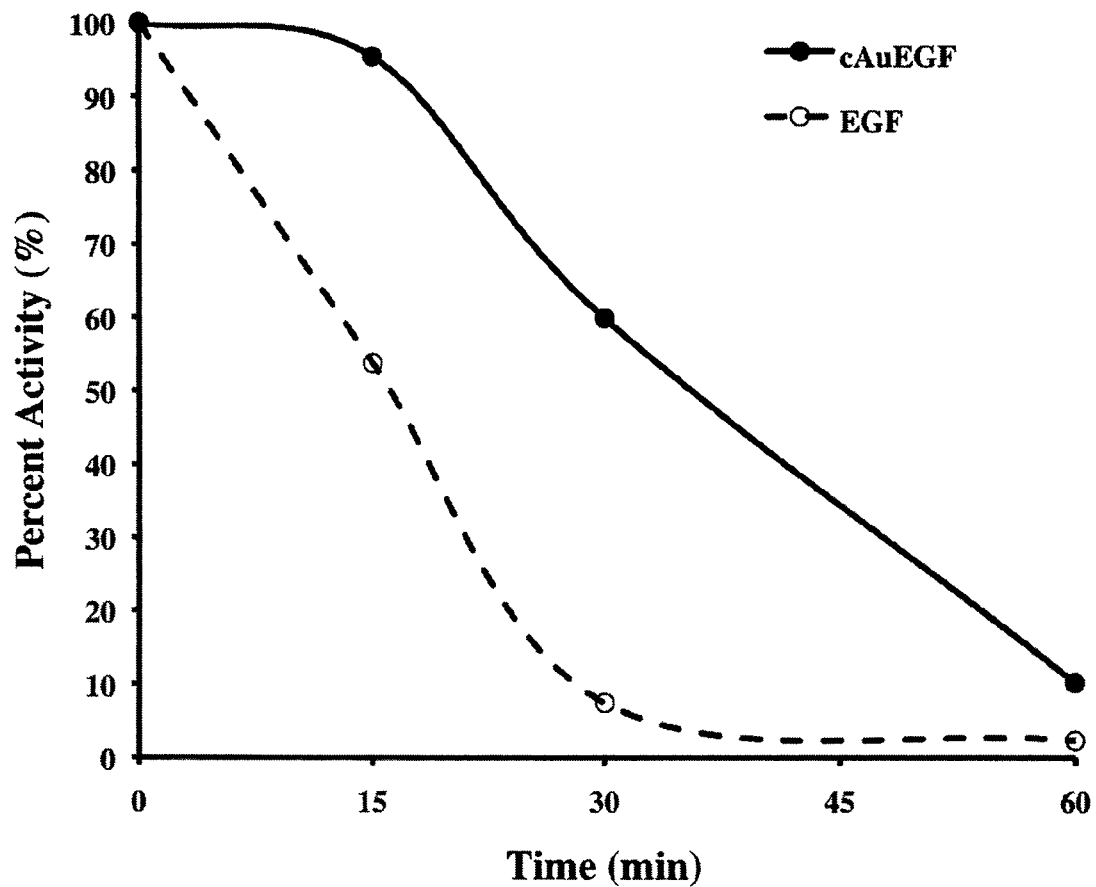
FIG. 3A provides a line graph showing time dependent denaturation of either soluble EGF or colloidal gold bound EGF in the generation of human EGF antigen for immunization.

As is known to those skilled in the art, heat denaturation of an antigen is often effective in altering a native, non-immunogenic antigen, such that it is able to elicit an immunogenic response. Heating helps to elicit an immune response by exposing epitopes that may otherwise be obstructed on the native antigens. Nevertheless, heat treatment does not change the protein/antigen completely (i.e., the protein sequence), but adequately alters the structure of the native protein to generate effective immunogens. Optimum heat treatment of a native antigen may in part preserve the native conformation of certain regions intact, but results in imparting immunogenicity to the antigen overall. Using the novel in vitro culture systems of the present invention (see details below), the heat-denatured antigens of the present invention are able to produce antibodies that recognize both native and heat treated antigens. Described in the invention are methods for heat treatment that do not destroy the native antigen epitopes, and surprisingly, what had been tested in an in vivo system for vaccines and other studies holds good for in vitro culture systems also. A time course of heat inactivation is established for each antigen and a correlation between time of heat inactivation and percent loss of activity is established (see for example, FIG. 3A).

The present invention comprises the use of the modified or denatured antigens as described above in culture systems that enable antigen uptake and processing by an antigen presenting cell and B-cell resulting in the generation of a human anti human antibody response. The method of the present invention produces some antibodies that recognize the denatured antigen and some antibodies that recognize the native (natural) antigen. The types of antibodies that are produced are generally in the IgM and IgG class.

The method of using a denatured form of an antigen to enable the in vitro production of fully human antibodies capable of recognizing the corresponding native antigens is an unanticipated result. It is expected that antibodies capable of recognizing the denatured antigen would be generated. However, it is surprising that the method of the present invention, using modified or denatured antigens in vitro, can produce antibodies that recognize the natural antigen.

In addition, the generation of a human anti human antibody response using a colloidal gold bound form of the antigen is also a novel and unanticipated result. Furthermore, the methods described herein have the unique ability to use naturally occurring breakdown products of a given antigen for immunization in the described culture system resulting in the generation of antibodies that recognize the native antigen.

As specifically discussed in the Examples, antigens are prepared for immunological presentation by various modification steps involving denaturation and incubation with a colloidal metal. The Examples demonstrate in detail how the TNF, Clostridium difficile (C. Dif) toxins A & B, IL-2, IL-4, and EGF antigens were prepared. In some cases, such as TNF, C. Dif Toxins, IL-2 and IL-4, the antigens were denatured. For example, the human TNF antigen was prepared by heat denaturation of either the soluble or a colloidal gold bound formulation of TNF. For IL-2 and IL-4, denaturation was achieved by merely binding the proteins to the surface of the colloidal gold nanoparticles. The end result of this treatment was the generation of antigenic forms of the human proteins.

In another example, a peptide, such as EGF, could also be rendered antigenic by merely binding it to the surface of the colloidal gold nanoparticles. Unlike the IL-2 and IL-4 examples, colloidal gold bound EGF retained its biologic activity and acquired an immunogenic phenotype on the particle.

As would be evident to those skilled in the art, although the Examples concern the antigens TNF, IL-2, IL-4 and EGF, similar techniques could be used for other antigens in accordance with the spirit of the present invention.

Another aspect of the technology is the use of nanoparticles or other crosslinking methods to generate a chimeric antigen that can be used to immunize human lymphocytes to generate human antibodies against both antigens. The methods enable manipulation of the culture system such that it facilitates class switching and the control over the class of antibodies that are produced.

The in vitro culture system herein described is flexible and may be manipulated to allow customization of the resultant human antibody. We have established that addition of cytokines such as IL-2, IL-21 and anti-CD-40, activates the antigen primed B cells to differentiate into antibody secreting cells. This combination of cytokine resulted in switching antigen specific antibody response from IgM to IgG. For the colloidal gold bound EGF antigen, changing these cytokines to a different combination such as IL-5, IL-10 and TGF-β, allows for the expression of yet another class of antibodies, namely IgA. Such manipulations are not possible in vivo, with transgenic mice, or with other in vitro technologies, such as phage display.

One aspect of the present invention further comprises fusion of species-specific B cells to a myeloma cell line creating a hybridoma. In a particular embodiment, for example, human B cells are fused to a murine/human heteromyeloma cell line resulting in the generation of human hybridomas secreting completely human monoclonal antibodies that not only bind the native human antigen, but may also neutralize the biologic action of the antigen. The production of the hybridomas may be scaled up and those secreting desired antibodies (for example neutralizing monoclonal antibodies) may be selected. Isolation of genes encoding fully species-specific monoclonal antibodies for expression and scale up can be done using standard technologies. In addition, human monoclonals can be made into proteins, carbohydrates and nucleic acid molecules.

An important aspect of the present invention is the development of a customizable methodology involving a unique culture system for producing monoclonal antibodies. In summary, the methodology involves the isolation of immunologically relevant cells such as peripheral blood B cells and mononucleocytes (PBMC), modification of the antigen, co-culturing the cells in antigen media, stimulation of antigen primed B cells and screening for the antibody, fusion and generation of hybridoma cultures, and identification and characterization of antibody secreting clones.

Described in the present invention is a unique culture system in which monocytes are differentiated into antigen presenting dendritic cells by culturing them with the modified antigens. In turn, these monocyte-derived dendritic antigen presenting cells provide cell-to-cell contact to induce the effective cloning of B cells and to induce an antibody response from these B cells. Furthermore, though not wishing to be bound by the following theory, the present inventors propose that differentiating monocytes act as antigen depots and provide effective antigen presentation as the antibody responses were in these cultures for two to three weeks even without additional antigen. Also, not wishing to be bound by the following theory, it is thought that monocytes secrete important growth factors and so, along with externally added stimulation factors, an enhanced growth environment is provided for B cells. Ultimately, the co-culturing of B cells along with the monocytes enables B cells to respond to antigen stimulation. Finally, although the above culture is preferred, the invention is not limited to this cell combination as other combinations of monocytes, T cells and B cells mediate the human antibody response, and we have seen that unpurified peripheral blood lymphocytes respond to the modified antigens in vitro to produce an antibody response, albeit to a lower level.

The preferred co-culture system of the present invention involves the use of at least two cell types that have a positive symbiotic relationship, resulting in the enhanced development of antibodies. However, it is not sufficient to simply combine monocytes and B cells with the expectation of enhanced immunological results. The ratio of B cells to monocytes is critical for good antibody responses. In an experiment keeping the B cell numbers constant, the number of monocytes were varied at ratios of 1:1, 1:2, and 1:5. In another set of experiments, the monocytes were kept constant and B cell numbers were varied such as 2:1 B cells to monocytes. Under all the conditions, cultures were microscopically observed for the number of plaque units formed, and only when one-part B cells with 5 part monocytes were used did the cultures appear active and productive.

In addition, changes in culture conditions, such as the modification of antigen, the amount of antigen added, the time period used for antigen priming, concentration of cytokine stimulants and combination of cytokines used and time used for incubation, all impact the response.

For example, cytokines used in the culture system include IL-2, IL-4, IL-5, IL-10, IL-21, TNF, anti-CD-40, CD-40L, TGF-beta, and GM-CSF. Furthermore, as described in the literature, the combinations are important since the function of the cytokine IL-4 antagonizes the function of IL-21.

The unique co-culture system of the present invention is novel for several reasons. First, monocytes can be differentiated into interstitial dendritic cells under current co-culturing conditions (in presence of anti-CD-40, IL-2, IL-21 in the stimulation media and TNF). TNF and anti-CD-40 enables the differentiation of monocytes into dendritic cells. The co-culture system herein described achieves the activation of B cells and differentiation of monocytes at the same time.

Second, differentiated monocytes present antigen to B cells and can be co-cultured for up to three weeks in an in vitro system (as evidenced by B cell antibody response).

Third, while the modified (i.e. heat denatured) antigen is taken up and presented to B cells, the process also triggers differentiation of monocytes into dendritic cells to promote the presentation of the human antigen to the B cells. The antigen presenting cells are created in the culture system, and this is an underlying reason that antigen-specific antibodies are produced in the culture system herein described.

Fourth, both self and non-self antigens which have been denatured including the alpha and beta form of the soluble IL-2 receptor, and *C. dif* toxins have generated antigen specific antibody responses in the above culture system, albeit the extent of antibody differentiation process may depend on the type/strength of signaling that is turned on. Finally, the system of the present invention is unique in that it can be used to develop antibodies to self and non-self antigens, which are not otherwise amendable to antibody response.

The culture system of the present invention mimics the stimulation of antigen primed B cells in vivo. In vivo, cytokines such as IL-2, IL-4, are secreted by T cells and activate antigen primed B cells to proliferate and recombine on their immunoglobulin locus to achieve class switching. By adding cytokines that are known to activate proliferation of B cells and immune response to the culture system, B cells were activated in vitro. Culturing the B cells in presence of antigen and cytokines resulted in differentiation of B cells into antibody secreting cells. In the absence of externally added cytokines, the antibody response was low. This suggested that it is necessary to add the T cell growth factors to the in vitro culture for the system to work. Stimulation is essential for an enhanced antibody response, since stimulation achieves a bystander effect on the B cells. This bystander effect helps maintain a viable culture, over four weeks, with continued antibody response.

These cytokines also regulate the type of signaling necessary to generate different classes of antibodies. While it is necessary to have IL-2, IL-4, and anti-CD-40, or to have IL-2, IL-21, and anti-CD-40, to generate IgG and IgM classes of antibodies, the combination of IL-2, IL-5, IL-10 and TGF-beta produced IgA antibodies. These combinations of cytokines are known to activate signaling which results in class switching in vivo but had not been successfully used in vitro until developed by the present inventors.

The culture systems of the present invention are flexible and amenable to changes during the process to alter the resultant antibodies obtained. The in vitro system allows for easy manipulation of the cytokine-signaling pathway by simply adding activators or inhibitors of a specific pathway into these cultures. The expression of cytokines over a period of time can be followed and serves as markers for changes in immune response and class switching. For example, as shown in Table II immunizing the B cell:monocyte co-culture with ΔTNF and stimulation with the IL-2/IL-21/anti-CD40 cocktail promoted the production of IL-10 and a fully human IgG antibody that recognized the native antigen. Thus, based on the present inventors work, it now becomes apparent that intervening with activators or inhibitors at any of the above pathways may alter the production of the resultant antibody. As a simple example, the addition of a neutralizing murine antibody that blocks the effect of the IL-10 in this system to block any IL-10-dependent signaling may alter the final antibody product.

Figure 9:
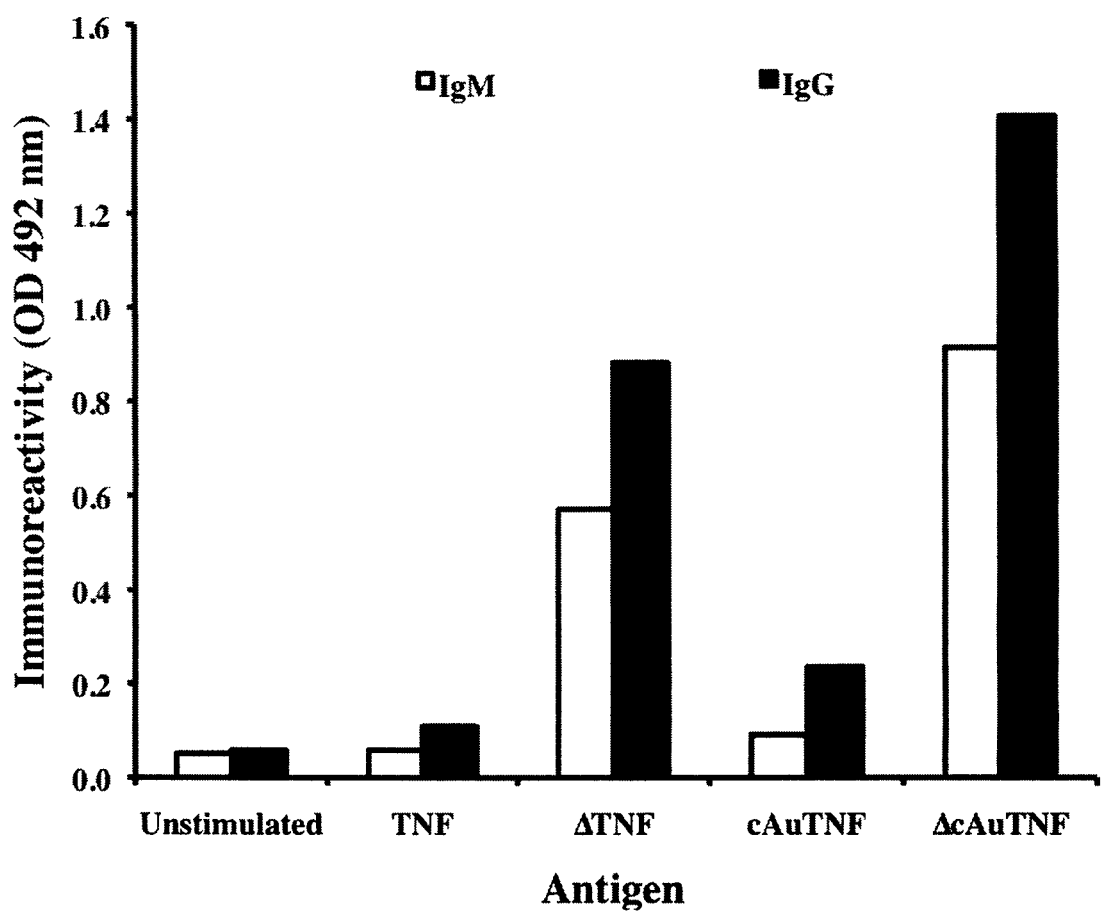
FIG. 9 provides data showing the induction of primary (IgM) and cytokine driven class-switched antibody responses following the immunization of B-cell/monocyte cultures with the heat denatured TNF. The presence of IgM confirms the generation of a de novo antibody response against the denatured TNF antigen, while the cytokine driven induction of class switching is confirmed by the presence of TNF specific-fully human IgG antibodies.
Figure 10:
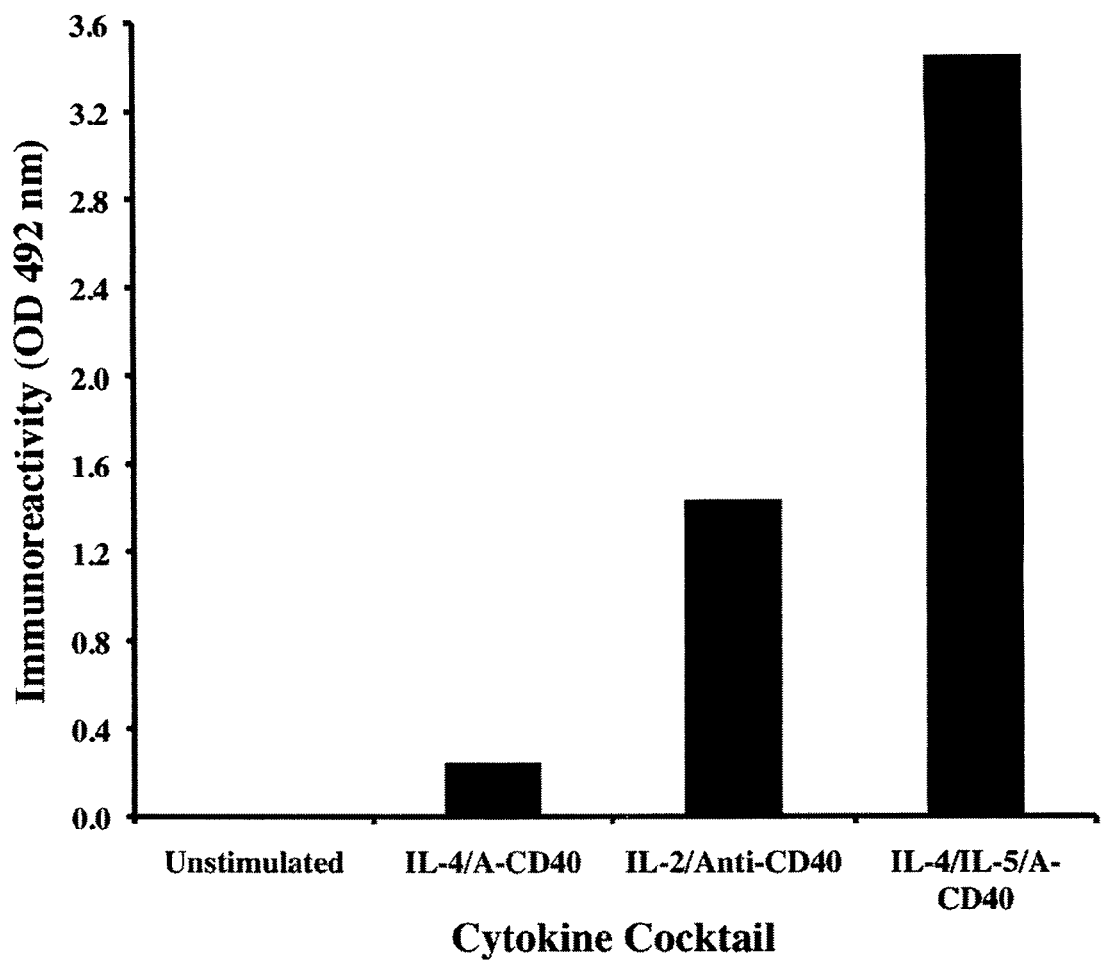
FIG. 10 provides data showing that the strength of class switching response may be controlled/customized by varying the cytokine cocktail.
Figure 11A:
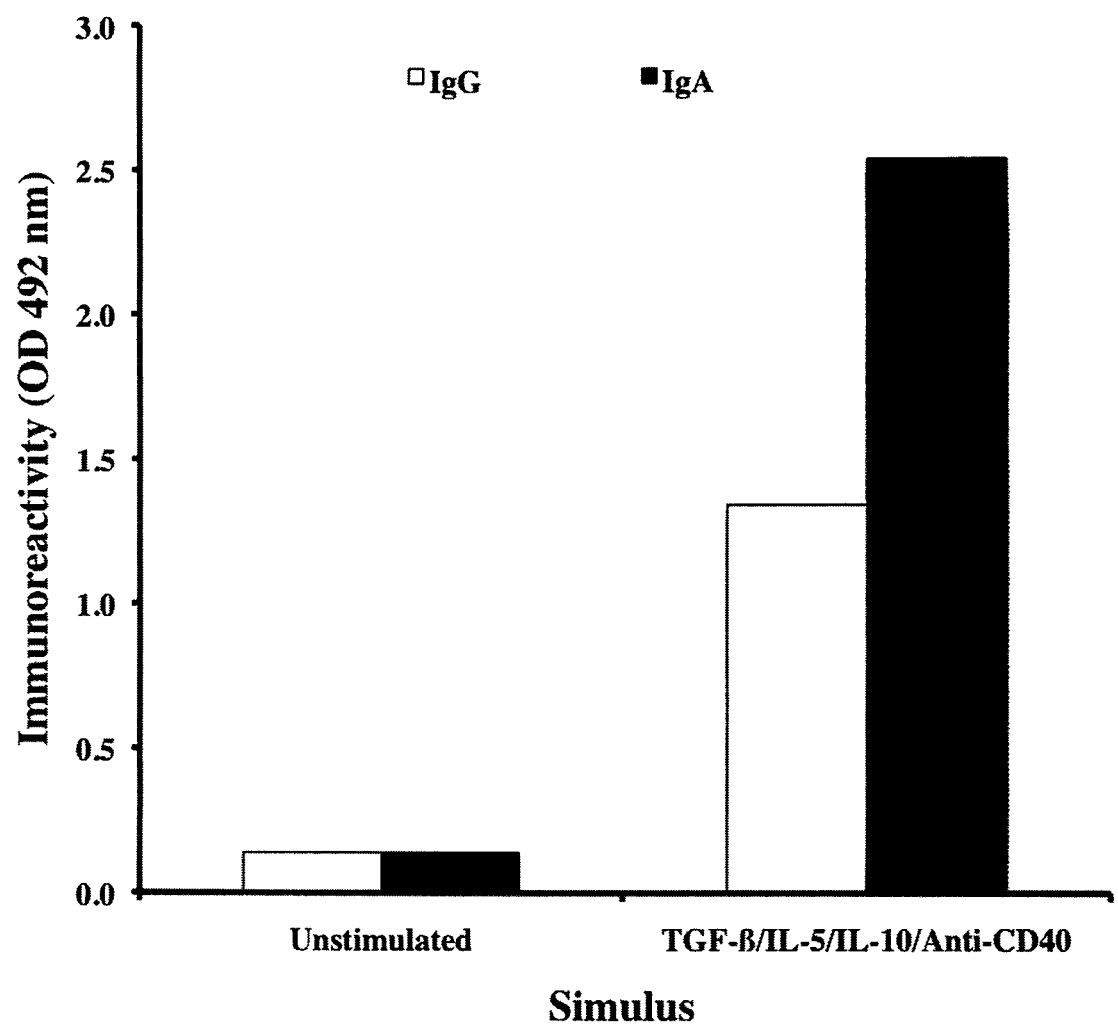
FIG. 11A shows the induction of EGF specific IgA and IgGs human antibodies.
Figure 11B:
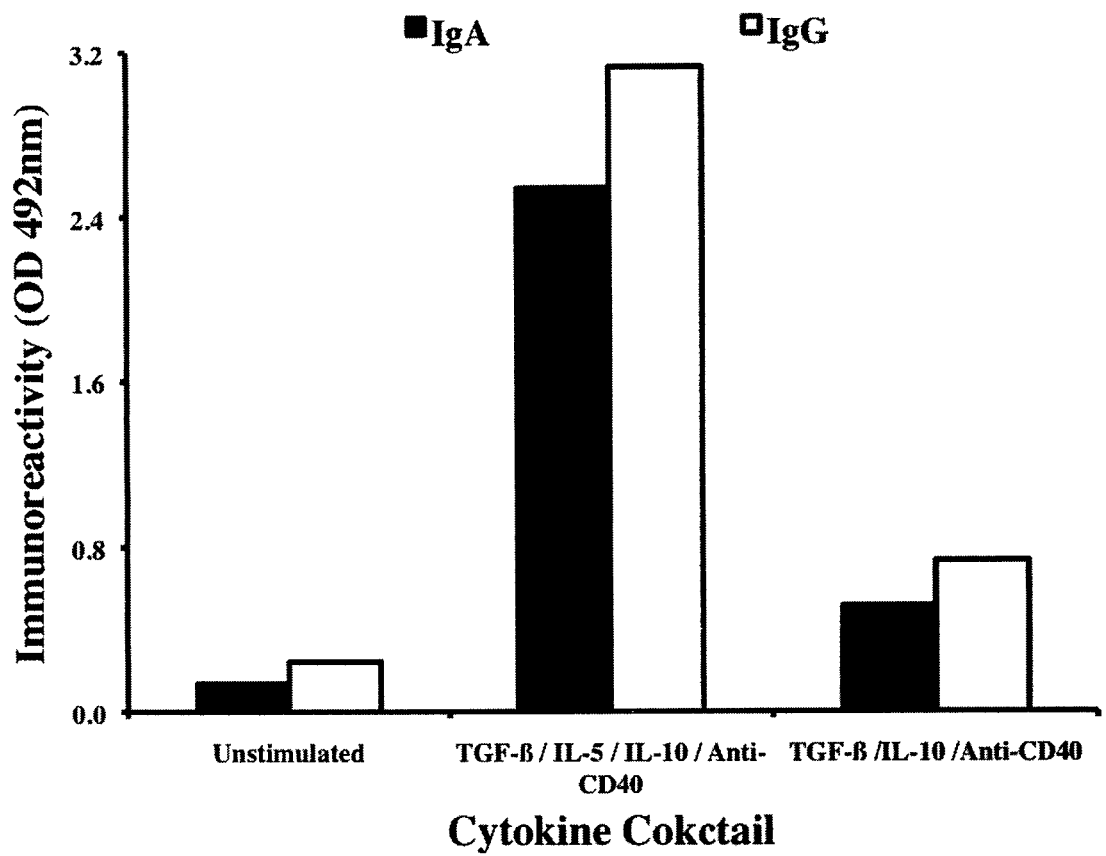
FIG. 11B reveals the effect of removing the cytokine IL-5 from the cocktail class switching response.

As an additional example of how the culture system may be customized, we demonstrated that by changing the cytokine cocktail shown in FIGS. 9 and 10 altered the strength and class of the human antibody response. For example, when IL-2, IL-21 and anti-CD-40 are combined with ΔTNF antigen, the culture system produced human anti human TNF antibodies of both IgG and IgM classes. In another experiment, when EGF was the antigen and IL-5, IL-10, anti-CD-40 and TGF-β were added as stimulants, human anti human IgA antibodies against human EGF were produced. These data suggest that in vitro class switching of human anti human antibody production depends on the culture conditions used. In effect, the data presented reveal that the current system generates fully human antibodies against putative self and non-self antigens. The resultant antibodies are of appropriate class and subclass to therapeutic use. Finally as shown in FIG. 11A, the antibody secreting B cells are fused with myeloma cells to generate stable cell lines that secreted monoclonal antibodies.

In certain alternative embodiments more than one antigen may be used to generate more than one type of antibody: for example, antigen preparation may involve co-binding the putative (first) antigen along with TNF (second antigen) and PEG-THIOL onto the surface of a colloidal gold nanoparticle. This preparation could be then denatured as described above and used to generate not only human anti human TNF antibodies, but also antibodies to the first antigen. Therefore, an additional advantage of the present invention is the ability to generate antibodies that are specific for multiple antigens.

In conducting the present studies, an additional discovery that was made was that certain proteins denature as they bind to the surface of colloidal metal nanoparticles. These proteins contain various chemical side groups that form chemical bonds with the colloidal metal that affects the conformation of the protein itself. For example IL-2 and IL-4 contain multiple sulfhydryl and disulfide groups that form dative covalent bonds with the atoms of gold on the surface of gold nanoparticles (see FIG. 3A). In the case of IL-2 and IL-4, the formation of these bonds destroys the conformation of the protein and results in a loss of immunologic detection and biologic activity. Gold-based denaturation is dependent on the specific proteins (i.e., some proteins may denature, while other do not).

As specifically discussed in the Examples, the efficacy of the antigens was assessed using an in vitro assay: a B cell/monocyte co-culture may be immunized with various forms of heat denatured human antigens; the cultures are then incubated with the antigens for a set period of time and subsequently exposed to the various stimuli (for example CD-40L, IL-2 and IL-21; the stimulation phase) to induce class switching.

In the past, due to lack of an effective antigen presenting system, an in vitro immune response using human lymphocytes in culture was not successful. By combining the unique colloidal gold nanotechnology approach and innovative culture system derived out of human peripheral blood mononucleocytes described herein, the present inventors were able to generate fully human anti human antibodies.

As described herein, colloidal metals, for example colloidal gold, act as unique carrier systems for antigen presentation. Due to the diversity of binding chemistries between various molecules and colloidal metals, this system allows for the preparation of a variety of species-specific antigens. In particular, use of colloidal gold is especially suited to the generation of human antibodies.

Proteins such as TNF alpha, a cytokine involved in the activation of B cells, can be made into effective antigens by binding to cAu (colloidal gold) and further denaturation by chaotropic treatments. Certain proteins, such as cytokines IL-2 and IL-4, are denatured upon binding to cAu. Instead of additional chaotropic treatments to denature these proteins, the cAu-protein complexes can be used directly in the culture system to elicit an immune response. Without some form of denaturation, molecules that are active in the immune response signaling cascade would not elicit an immune response.

Molecules not involved in the immune response signaling cascade do not need denaturation to elicit an immune response and may be transformed into effective antigens by binding to cAu and remaining active. For example, EGF is a small molecular weight peptide hormone that, in its soluble form, does not elicit an immune response in the presently described culture system. In contrast, the active colloidal gold bound-EGF formulation does elicit an immune response. This is most likely due to increased uptake of the cAu-EGF complex compared to the soluble protein, therefore increasing the effective concentration of EGF in the antigen presenting cells. This opens up a new possibility for human therapeutic molecules, which are not immunogenic and occur in low concentrations.

The current culture system is also flexible enough to work at lower protein concentrations and with multiple antigens. For example, by presenting TNF on the same cAu that carries an inactivated cytokine, the immune response cultures could be stimulated to function at their maximum. The Examples demonstrate in detail the preparation of a chimeric cAu antigen comprising TNF and an inactivated cytokine, IL-2. Presentation of more than one antigen on one carrier system is currently not possible with any other technology.

The present invention further includes using the above methods to generate fully human monoclonal antibodies with different functionalities. In one example, the human soluble IL-2 receptor was used as the human antigen. The receptor was prepared by heat denaturation and used to immunize the human B-cell/monocyte co-culture. As shown in FIG. 9, the fully human antibodies generated possess different functionalities.

Colloidal Metals

One aspect of the present invention is directed to methods and compositions comprising colloidal metals as vectors for the unique presentation of antigens. Specifically, preferred compositions are used in methods for immunostimulation. Methods for stimulating the immune system resulting in the elicitation of specifically desired and species specific antibodies comprise administering colloidal metal sol compositions comprising the antigen, optionally combined with PEG, preferably derivatized-PEG, more preferably, thiol-derivatized polyethylene glycols. Though not wishing to be bound by any particular theory, it is thought that use of such compositions results in optimal and effective antigen presentation.

The compositions of the invention preferably comprise a colloidal metal sol, derivatized compounds and one or more denatured protein antigens. The antigens may be biologically active agents that can be used for immunostimulation. In preferred embodiments, one or more antigens are denatured, associated with or bound directly or indirectly to the colloidal metal and subsequently denatured. Association and binding includes covalent and ionic bonds and other weaker or stronger associations that allow for long term or short term association of the derivatized-PEG, agents, and other components with each other and with the metal sol particles.

Any colloidal metal can be used in the present invention. Colloidal metal includes any water-insoluble metal particle or metallic compound dispersed in liquid water, a hydrosol or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, pal ladium, indium, tin, tungsten, rhenium, platinum, and gadolinium. The metals are preferably provided in ionic form, derived from an appropriate metal compound, for example the $Al^{3+}$, $Ru^{3+}$, $Zn^{2+}$, $Fe^{3+}$, $Ni^{2+}$ and $Ca^{2+}$ ions.

A preferred metal is gold, particularly in the form of $Au^{3+}$ which is converted to $Au^0$ by its reduction with sodium citrate. In one embodiment, the colloidal gold particles have a negative charge at an approximately neutral pH. It is thought that this negative charge prevents the attraction and attachment of other negatively charged molecules. In contrast, positively charged molecules are attracted to and bind to the colloidal gold particle. The colloidal gold is employed in the form of a sol containing gold particles having a range of particle sizes, though a preferred size is a particle size of approximately 30 to 40 nm.

Another preferred metal is silver, particularly in a sodium borate buffer, having the concentration of between approximately 0.1% and 0.001%, and most preferably, approximately a 0.01% solution. Preferably, the color of such a colloidal silver solution is yellow and the colloidal particles range from 1 to 40 nm. Such metal ions may be present in the complex alone or with other inorganic ions.

The antigens of the present invention can be any biological factors or fragments of biological factors such as antibodies, proteins, lipids, nucleic acids or carbohydrates; nucleic acids, antibodies, proteins, lipids, nutrients, cofactors, nutriceuticals, anesthetics, detection agents or an agent that has an effect in the body.

The following are non-limiting examples of some of the antigens that can be used in the present invention. One type of agent that can be employed in the present invention includes biological factors including, but not limited to, cytokines, growth factors, fragments of larger molecules that have activity, and cellular communication molecules. Examples of such agents include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10

("IL-10"), Interleukin-11 ("IL-11"), Interleukin-12 ("IL-12"), Interleukin-13 ("IL-13"), Interleukin-15 ("IL-15"), Interleukin-16 ("IL-16"), Interleukin-17 ("IL-17"), Interleukin-18 ("IL-18"), Type I Interferon, Type II Interferon, Tumor Necrosis Factor ("TNFα"), Transforming Growth Factor-α ("TGF-a"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor-β ("TGF-β"), fibroblast growth factor, and angiostatin, endostatin, and GABA.

Another type of antigen includes hormones. Examples of such hormones include, but are not limited to, growth hormone, insulin, glucagon, parathyroid hormone, luteinizing hormone, follicle stimulating hormone, luteinizing hormone releasing hormone, estrogen, and derivatives and analogs of hormones.

Yet another type of antigen includes pharmaceuticals. Any type of pharmaceutical agent can be employed in the present invention. For example, anti-inflammatory agents such as steroids and nonsteroidal anti-inflammatory agents, soluble receptors, antibodies, antibiotics, analgesics, angiogenic and anti-angiogenic agents, and COX-2 inhibitors, can be employed in the present invention.

Another type of antigen includes nucleic acid-based materials. Examples of such materials include, but are not limited to, nucleic acids, nucleotides, DNA, RNA, tRNA, mRNA, sense nucleic acids, antisense nucleic acids, ribozymes, DNAzymes, protein/nucleic acid compositions, SNPs, oligonucleotides, vectors, viruses, plasmids, transposons, and other nucleic acid constructs known to those skilled in the art.

Other antigens that can be employed in the invention include, but are not limited to, lipid A, phospholipase A2, endotoxins, staphylococcal enterotoxin B and other toxins, heat shock proteins, carbohydrate moieties of blood groups, Rh factors, cell surface receptors, antibodies, cancer cell specific antigens; such as MART, MAGE, BAGE, and HSPs (Heat Shock Proteins), radioactive metals or molecules, detection agents, enzymes and enzyme co-factors.

Another component of the compositions of the present invention comprises glycol compounds, preferably polyethylene glycol (PEG), more preferably derivatized PEG. The present invention comprises compositions comprising derivatized PEG, wherein the PEG has a molecular weight range of 5,000 to 30,000 daltons. Derivatized PEG compounds are commercially available from sources such as Shearwater Corporation, Huntsville, Ala. PEG compounds may be difunctional or monofunctional, such as methoxy-PEG (mPEG). Activated derivatives of linear and branched PEGs are available in a variety of molecular weights. As used herein, the term "derivatized PEG(s)" or "PEG derivative(s)" means any polyethylene glycol molecule that has been altered with either addition of functional groups, chemical entities, or addition of other PEG groups to provide branches from a linear molecule. Such derivatized PEGs can be used for conjugation with biologically active compounds, preparation of polymer grafts, or other functions provided by the derivatizing molecule.

One type of PEG derivative is a polyethylene glycol molecule with primary amino groups at one or both of the termini. A preferred molecule is methoxy PEG with an amino group on one terminus. Another type of PEG derivative includes electrophilically activated PEG. These PEGs are used for attachment of PEG or methoxy PEG (mPEG), to proteins, liposomes, soluble and insoluble polymers and a variety of molecules. Electrophilically active PEG derivatives include succinimide of PEG propionic acid, succinimide of PEG butanoate acid, multiple PEGs attached to hydroxysuccinimide or aldehydes, mPEG double esters (mPEG-CM-HBA-NHS), mPEG benzotriazole carbonate, mPEG propionaldehyde, and mPEG acetaldehyde diethyl acetal.

A preferred type of derivatized PEG comprises thiol derivatized PEGs, or sulfhydryl-selective PEGs. Branched, forked or linear PEGs can be used as the PEG backbone that has a molecular weight range of 5,000 to 40,000 daltons. Preferred thiol derivatized PEGs comprise PEG with maleimide functional group to which a thiol group can be conjugated. A preferred thiol-PEG is methoxy-PEG-maleimide, with PEG molecular weight of 5,000 to 40,000 daltons.

Use of heterofunctional PEGs, as a derivatized PEG, is also contemplated by the present invention. Heterofunctional derivatives of PEG have the general structure X-PEG-Y. When the X and Y are functional groups that provide conjugation capabilities, many different entities can be bound on either or both termini of the PEG molecule. For example, vinylsulfone or maleimide can be X and an NHS ester can be Y. For detection methods, X and/or Y can be fluorescent molecules, radioactive molecules, luminescent molecules or other detectable labels. Heterofunctional PEG or monofunctional PEGs can be used to conjugate one member of a binding pair, such as PEG-biotin, PEG-Antibody, PEG-antigen, PEG-receptor, PEG-enzyme or PEG-enzyme substrate. PEG can also be conjugated to lipids such as PEG-phospholipids.

The formulations may conveniently be presented in unit dosage form and may be prepared by conventional pharmaceutical techniques. Pharmaceutical formulation compositions are made by bringing into association the metal sol vectors and the pharmaceutical carrier(s) or excipient(s). In general, the formulations are prepared by uniformly and intimately bringing into association the compositions with liquid carriers or finely divided solid carriers or both, and then, if necessary, shaping the product.

Examples of immunostimulating molecules suitable for use in the cytokine cocktail include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), Interleukin-15 ("IL-15"), Interleukin-18 ("IL-18"), Interleukin-20 ("IL-20"), Interleukin-21 ("IL-21"), IL2 receptor alpha and IL2 receptor beta, lipid A, phospholipase A2, endotoxins, staphylococcal enterotoxin B and other toxins, Type I Interferon, Type II Interferon, Tumor Necrosis Factor ("TNF-α"), TNF receptor I and II, Transforming Growth Factor-β ("TGF-β") Lymphotoxin, Migration Inhibition Factor, Granulocyte-Macrophage Colony-Stimulating Factor ("GM-CSF"), Monocyte-Macrophage CSF, Granulocyte CSF, vascular epithelial growth factor ("VEGF"), Angiogenin, transforming growth factor ("TGF-a"), heat shock proteins, carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE; flt3 ligand/receptor system; B7 family of molecules and receptors; CD40 ligand/receptor; and immunotherapy drugs, such as AZT; and angiogenic and anti-angiogenic drugs, such as angiostatin, endostatin, and growth factors (including but not limited to basic fibroblast growth factor (bFGF), epidermal growth factor (EGF), platelet derived growth factor (PDGF)), cytokines and cytokine receptors, membrane receptors (including but not limited to G protein coupled receptors, Her 2 Neu, CD19, CD22, CD20, CD2), hormones (including but not limited to Follicular Stimulating Hormone, Estrogen, Progesterone, Leutinizing Hormone) and transcription factors (including but not limited to NF-Kappa B, ETS family of protein, and CREB family of protein).

The activation of the in vitro immune response may result in a stimulation or suppression of other components of the culture system, leading to an overall stimulation or suppression of the immune response. For ease of expression, stimulation of immune components is described herein, but it is understood that all responses of immune components are contemplated by the term stimulation, including, but not limited to, stimulation, suppression, rejection and feedback activities.

The immune component that is effected may have multiple activities, leading to both suppression and stimulation or initiation or suppression of feedback mechanisms. The present invention is not to be limited by the examples of immunological responses detailed herein, but contemplates component-specific effects in all aspects of the immune system.

The activation of each of the components of the immune system may be simultaneous, sequential, or any combination thereof. In one embodiment of a method of the present invention, multiple component-specific immunostimulating modified or denatured antigens are administered simultaneously. In this method, the immune system is simultaneously stimulated with multiple separate preparations, each containing a composition comprising a component-specific immunostimulating modified or denatured antigen. Preferably, the composition comprises the component-specific immunostimulating modified or denatured antigen associated with colloidal metal. More preferably, the composition comprises the component-specific immunostimulating modified or denatured antigen associated with colloidal metal of one sized particle or of different sized particles and an antigen. Most preferably, the composition comprises the component-specific immunostimulating modified or denatured antigen associated with colloidal metal of one sized particle or of differently sized particles, antigen and PEG or PEG derivatives.

As used herein, the term "immunologically relevant cells" includes, but is not limited to, B cells, neutrophils, eosinophils, basophils, lymphocytes, monocytes, leukocytes, and T cells.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Human Antigens

Figure 2A:
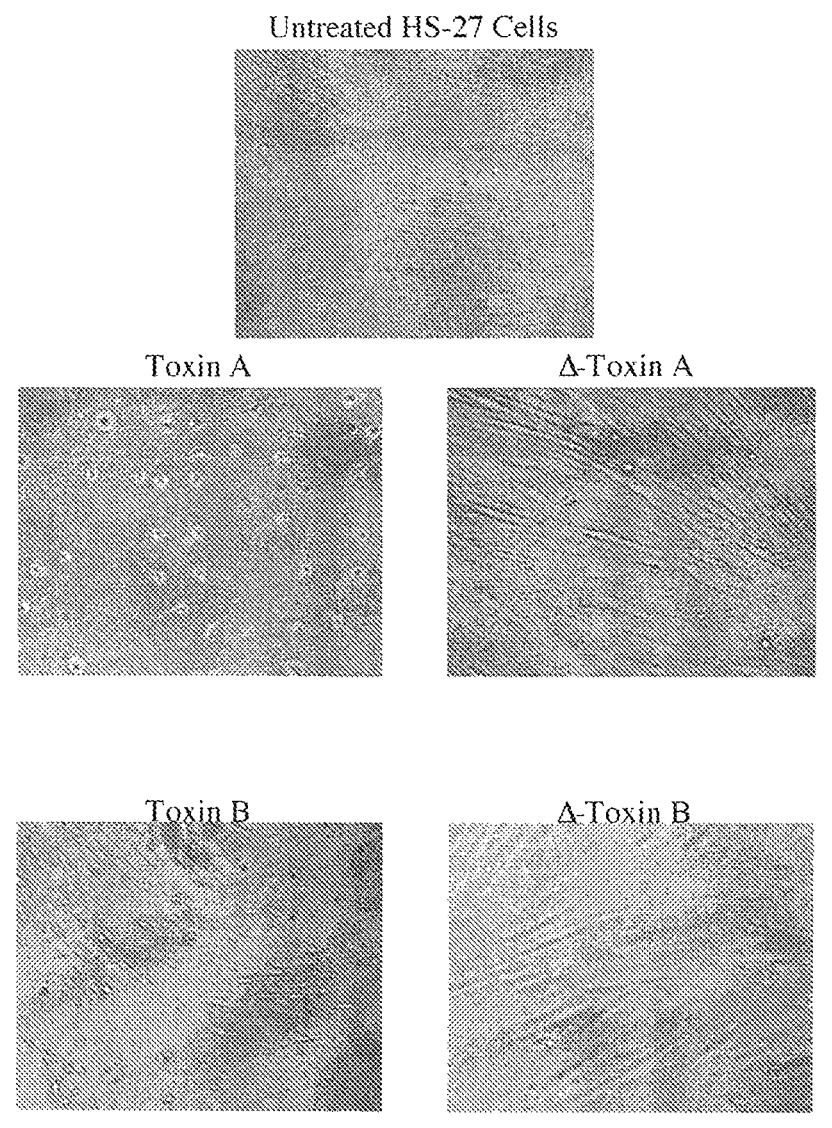

TNF, C. Dif. Toxins (A and B), Soluble IL-2 Receptor Subunits (α and β) and EGF: TNF and cAu-TNF at 137 μg/mL in complete media (RPMI-1640 with 10% fetal bovine serum and 1% antibiotic) were heat denatured for 5 minutes at 95° C. (FIG. 1). 1-20 μg of the C. Dif Toxins (A and B; FIG. 2A) as well as the soluble IL-2 receptor subunits (alpha and beta) were also heated to 95° C. until loss of bioactivity was demonstrated. IL-2 and IL-4 (FIG. 2B; see below for preparation) were denatured by directly binding them to colloidal gold nanoparticles. For EGF (FIG. 3A) the peptide or its colloidal gold bound variant (see below for preparation) were heated for 95° C. for various amounts of time until immunologic activity, as determined by ELISA, was lost. After denaturation, the tubes were kept on ice until the antigen was added to the culture. Untreated TNF, cAu-TNF and EGF were also kept on ice and used as controls.

IL-2 and IL-4 (FIG. 2B; Table I):

IL-2: The pH of cAu was adjusted to 8.0 with 100 mM Tris. IL-2 was added to 2 mL of pH-adjusted cAu at a final concentration of 1 μg/mL and incubated for 1 hr at 4° C. After incubation, 10 μg/mL 5K PEG-SH (Shearwater Polymers, San Carlos, Calif.) was added to the sample and incubated for an additional 15 min. The samples were then centrifuged at 10,000 rpm for 10 minutes. The supernatant and pellets were separated, and the pellets were resuspended to a total volume of 2 mL in complete media (RPMI-1640 with 10% fetal bovine serum and 1% antibiotic). To determine the amount of IL-2 activity, the supernatants (free IL-2) and resuspended pellets (cAu-bound IL-2) were then measured using the IL-2 CytELISA (CytImmune Sciences, Inc, Rockville Md.). The amount of protein bound and inactive on the cAu was estimated from the actual amount added minus the amount active and free measured in the supernatant.

As a control for denatured cAu-IL-2, 1-2 μg/mL soluble IL-2 in complete media was heat denatured for 60 minutes at 95° C. To determine the amount of IL-2 activity, the heat-denatured sample was measured using the IL-2 CytELISA (CytImmune Sciences, Inc, Rockville Md.). cAu-IL2 and heat denatured soluble IL-2 were stored on ice until the antigen was added to the culture.

IL-4: The pH of cAu (lot 52) was adjusted to pH 10 using 0.1M NaOH. cAu supernatant was prepared by centrifuging colloidal gold (lot 52) at 14,000 rpm for 10 min, retaining the liquid and discarding the colloidal gold pellet. The supernatant had an initial pH of ≈4.0. The supernatant was adjusted to pH 10 using 0.1 N NaOH.

IL-4 was diluted to 2 μg/mL in pH adjusted supernatant (2 mL total), added to 2 mL of pH adjusted cAu (1 μg/mL final concentration) and incubated for 1 hr at 4° C. After incubation, 10 μg/mL 5K PEG-SH (Shearwater Polymers, San Carlos, Calif.) was added to the sample and incubated for an additional 15 min. The samples were then centrifuged at 10,000 rpm for 10 minutes. The supernatant and pellets were separated, and the pellets were resuspended to a total volume of 2 mL in complete media (RPMI-1640 with 10% fetal bovine serum and 1% antibiotic). To determine the amount of IL-4 activity, the supernatants (free IL-4) and resuspended pellets (cAu-bound IL-4) were then measured using the IL-4 CytELISA (CytImmune Sciences, Inc, Rockville Md.). The amount of protein bound and inactive on the cAu was estimated from the actual amount added minus the amount active and free measured in the supernatant.

As a control for denatured cAu-IL-4, 1-2 μg/mL soluble IL-4 in complete media was heat denatured for 15 minutes at 95° C. To determine the amount of IL-4 activity, the heat denatured sample was measured using the IL-4 CytELISA (CytImmune Sciences, Inc, Rockville Md.). cAu-IL4 and heat denatured soluble IL-4 were stored on ice until the antigen was added to the culture.

EGF: The pH of cAu (lot 21, ~12 nm) was adjusted to 7.0 with 100 mM Tris. EGF was added to 20 mL of pH adjusted cAu at a final concentration of 6 μg/mL and incubated for 1 hr at 4° C. The samples were then centrifuged at 10,000 rpm for 45 minutes. The supernatant and pellets were separated, and the pellets were resuspended to a total volume of 2 mL in complete media (RPMI-1640 with 10% fetal bovine serum and 1% antibiotic). To determine the amount of EGF activity, the supernatants (free EGF) and resuspended pellets (cAu-bound active EGF) were then measured using the EGF duoset Elisa (R&D systems Inc., Minneapolis, Minn.). The % recovered was calculated by comparing the total amount assayed to the actual amount added.

Figure 3B:
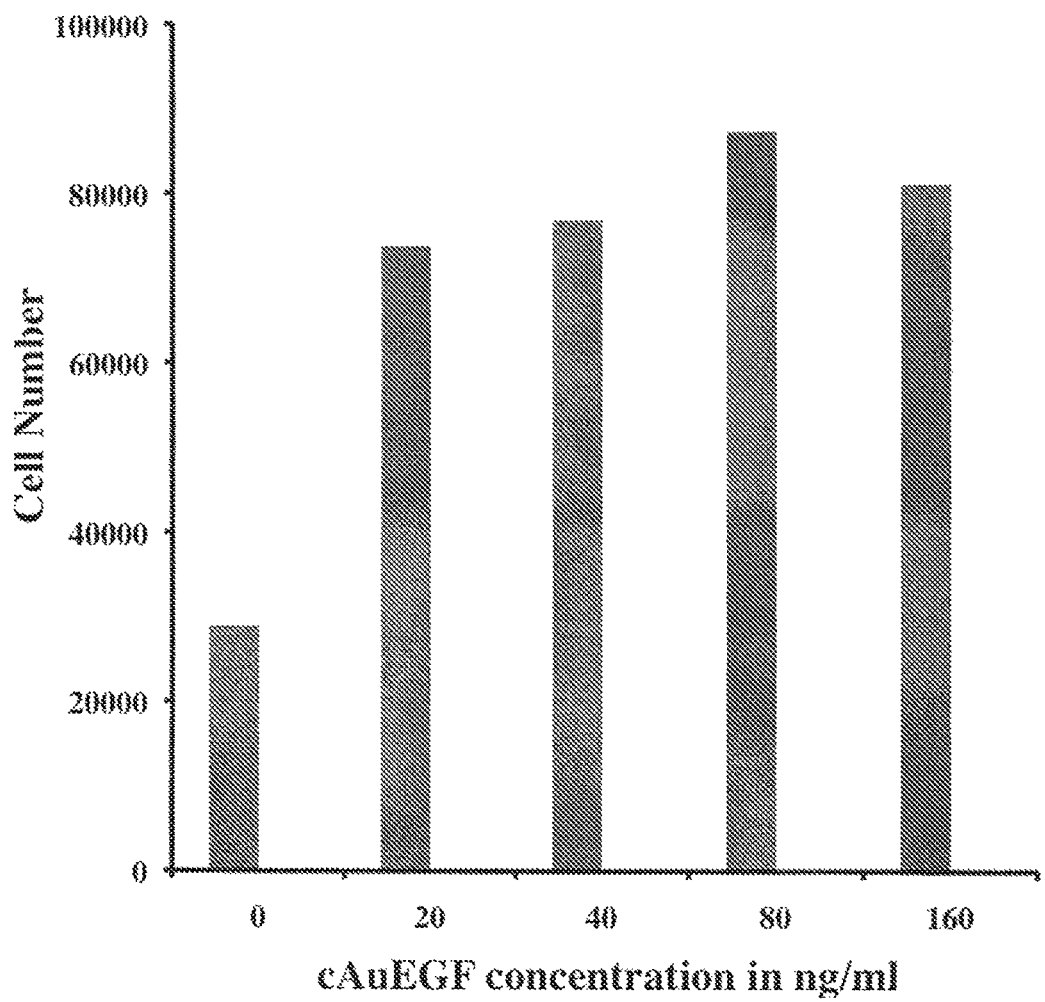
FIG. 3B provides evidence that an alternative human antigen formed by binding EGF to the surface of colloidal gold nanoparticles retains its bioactivity as shown by its ability to stimulate the proliferation of MCF-7 cells.

As a control for cAu-EGF, soluble EGF at 6 μg/mL in complete media was used. Biologic activity of the colloidal gold bound EGF was demonstrated by its reported ability to stimulate the in vitro proliferation of the human breast cancer cell line MCF-7. In this study, 5000 MCF-7 cells were plated in a 12-well plate. Subsequently, known quantities of the cAu-EGF were added to culturing MCF-7 cells. After 7 days the cells were harvested and cell number was determined using a Coulter Counter. The data presented in FIG. 3B demonstrate the cAu-EGF still possessed the known ability of EGF to induce the proliferation of MCF-7 cells. For the in vitro immunization studies, soluble EGF was stored on ice until the antigen was added to the culture as a control.

Chimeric Antigen: IL-2 and TNF (FIG. 4A):

The pH of cAu (lot 52) was adjusted to 8.0 with 100 mM Tris. IL-2 and TNF were added to 1 mL of pH adjusted cAu at a final concentration of 1.5 μg/mL and 100 ng/mL, respectively. The sample was incubated for 1 hr at 4° C. After incubation, 10 μg/mL 5K PEG-SH (Shearwater Polymers, San Carlos, Calif.) was added to the sample and incubated for an additional 15 min. The samples were then centrifuged at 10,000 rpm for 10 minutes. The supernatant and pellets were separated, and the pellets were resuspended to a total volume of 2 mL in complete media (RPMI-1640 with 10% fetal bovine serum and 1% antibiotic).

To demonstrate the presence of both proteins on the same gold nanoparticles, a cross antibody ELIA was done. For this assay, colloidal gold nanoparticles labeled with IL-2 alone served as a control for the gold nanoparticles containing both cytokines Both preparations were added to an ELISA plate coated with a monoclonal against TNF. After incubating the samples for two hours, the plate was washed and a rabbit anti IL-2 antibody was added to all wells. After another incubation period, an enzyme labeled goat anti-rabbit antibody was added to all the wells and the plate incubated for an additional hour. After a final wash, a substrate was added to all the wells and the resultant color measured using a plate reader. The data shown in FIG. 4B demonstrates that only the TNF/IL-2 chimera generated significant color, demonstrating the presence of both proteins on the same particle. The chimera was subsequently denatured by heating as described above.

Example 2

PBMC Isolation, Purification and Immunization

Isolation of Peripheral Blood Mononucleocytes (PBMC):

Buffy coat consists of monocytes, B cells, T cells and NK cells red cells. Total number of cells in a buffy coat is around 500–1000×106 in a volume of 50 ml. Peripheral blood mononucleocytes are separated from red cells upon Ficoll gradient centrifugation. Buffy coat cells were diluted with Hanks balanced salt solution (HBSS) 1:3. Diluted cells were then layered onto the Ficoll and centrifuged at 1600-rpm (800 g) for 30 minutes. Centrifugation separated mononuclear cells in the inter phase and red cells were in the pellet. PBMC were collected from the inter phase and used as the source material for isolation of B-lymphocytes and monocytes.

Isolation of B-Lymphocytes and Monocytes:

B cells and monocytes were isolated using CD19 or CD14 magnetic beads Miltenyi Biotec (Auburn, Calif.). Briefly, PBMC cells were washed with (magnetic cell sorting) MACS buffer (PBS, 0.5% BSA and 2 mM EDTA) and labeled with magnetic beads coated with antibodies to Human CD19 or CD14 molecules. Labeled cells were separated on LS column and CD19 and CD14 positive cells were collected. B cells and monocytes thus isolated were labeled with FITC CD19 or PE CD14 BD Biosciences (San Jose Calif.) and subjected to FACS analysis and found to be 90-95% pure.

In Vitro Immunization, Culture and Class Switching (FIGS. 5-8):

B cells and monocytes were resuspended in culture media and (RPMI-1640 with 10% fetal bovine serum and 1% antibiotic) seeded in 24-well plates at 1:5 ratios. 25-100 μl of the respective antigens and controls detailed above were added to separate wells. Cells were cultured at 37° C. and 5% $CO_2$ for 4-5 days. Subsequently, antigen media was replaced with stimulation media (complete media containing 20 ng/ml IL-21, 20 ng/ml IL-2, and 10 μg/ml anti-CD40) and cultured for three weeks. Every week the media was replaced with fresh stimulation media. The stimulation media may be modified to contain additional cytokines to control the predominant type of antibody produced during class switching.

Direct ELISA to Test Human Anti Antigen Antibody and Cytokine Production:

Media collected from cultures were tested for antigen specific human anti human antibodies by ELISA. 96-well flat bottom immuno plates (Nalge NUNC International) were coated with 5 μg/ml native antigen overnight at room temperature. ELISA plates were washed in a plate washer and blocked with diluent (PBS containing 1% BSA and 0.05% Tween). The culture media to be tested was diluted 1:2 in the diluent and added to the wells. Plates were incubated at room temperature overnight and washed. Alkaline phosphatase labeled Anti Human IgM and IgG were used to detect Human Anti Human antigen specific antibody and developed with Oxoid-AMP substrate DAKO (Carpinteria, Calif.). Absorbance of the alkaline phosphatase reaction was measured at 492 nm using a Molecular Devices Spectramac 340 PC.

Media samples generated from similar studies were analyzed for cytokine production. The samples were analyzed using multiplex technology (Pierce Chemical Company).

Culturing Hetero-myeloma K6H6Cells:

Hetero-myeloma K6H6 was purchased from ATCC. One vial containing $5.7 \times 10^6$ cells were thawed to room temperature and added in a T25 flask and cultured in complete media containing 10% serum and 1% antibiotic for two days. At the end of this period, the cells were spun down in a 15 mL tube and counted. $32.95 \times 10^6$ cells were equally distributed into two T75 flasks and expanded. $98.9 \times 10^6$ cells were collected from these two flasks. Cells were maintained at 200,000 cells/ml for further use.

Generation of Hybridoma:

B cells and monocytes were immunized with human antigens and antigen controls for the first week. Subsequently, antigen media was changed to stimulation media. Antigen primed B cells were removed from the culture dish and spun down in serum free media. Hetero-myeloma cells from the culture were also spun down and washed in serum free media. Serum coats the cells and inhibits the PEG fusion, therefore, it is necessary to perform the fusion in serum free media.

PEG Fusion:

Short duration of PEG exposure to the cells results in limited breakage and fusion of cells. Myeloma cells and B cells were taken in 1:2 ratio. Myeloma cells and B cells were spun down in serum free media. 1 mL of pre-warmed PEG 1540 (Roche) is slowly added to the tube containing cells. With a pipette tip, the pellet is dispersed and mixed in with the PEG. With the cells at 37° C., warm serum free media is added at the following volumes and durations: 1 mL for 30-60 sec, 3 mL for 30-60 sec, and 16 mL for 30-60 sec. After a further incubation of 5 min at 37° C., the cells are spun down in selection media (50×HAT, antibiotic/antimycotic 100×, serum, hybridoma cloning factor (Bio Varies), 10 mL RPMI, and sodium pyruvate).

Selection:

Fused cells are grown in selection media containing HAT. HAT stands for hypoxanthine, aminopterin and thymidine. Aminopterin blocks the nucleotide synthesis by inhibiting the enzyme DHFR (dihydrofolate reductase). Alternate pathway of nucleotide synthesis operates via the enzyme HGPRT. In the absence of this enzyme and in the presence of aminopterin in the media, nucleotide synthesis is blocked in myeloma cells. B cells make the enzyme HGPRT. Therefore, when the fusion of B cells and myeloma cells is successful, the resulting clone is able to survive in the selection media. B cells that are not fused but can still survive because they do make HGPRT do not live longer than the myeloma cells. Culture supernatants from the actively growing clones are tested for the presence of Human Anti Human antigen antibody.

Limiting Dilution:

The purpose of limiting dilution is two fold. The first is to separate non-antibody secreting cells from the colony, and the second is to make single cell clones from antibody-secreting cells of known specificity with isotype and affinity determined. In order to achieve this, the positive hybridoma clones from 96-well plates are diluted in such a way that 100 µl in the 96-well plate will have 10, 5, 2 and one cell in each well. Cells are grown to confluence and tested for antibody secretion. Positive clones from plates containing one cell per well have a greater chance of being single clones. The process limiting dilution is repeated to obtain a clone that is growing steadily and producing antibody. Aliquots of clones that are positive are frozen after every passage.

Example 3

Generation of a Human Antibody Response to Human TNF

Figure 5A:
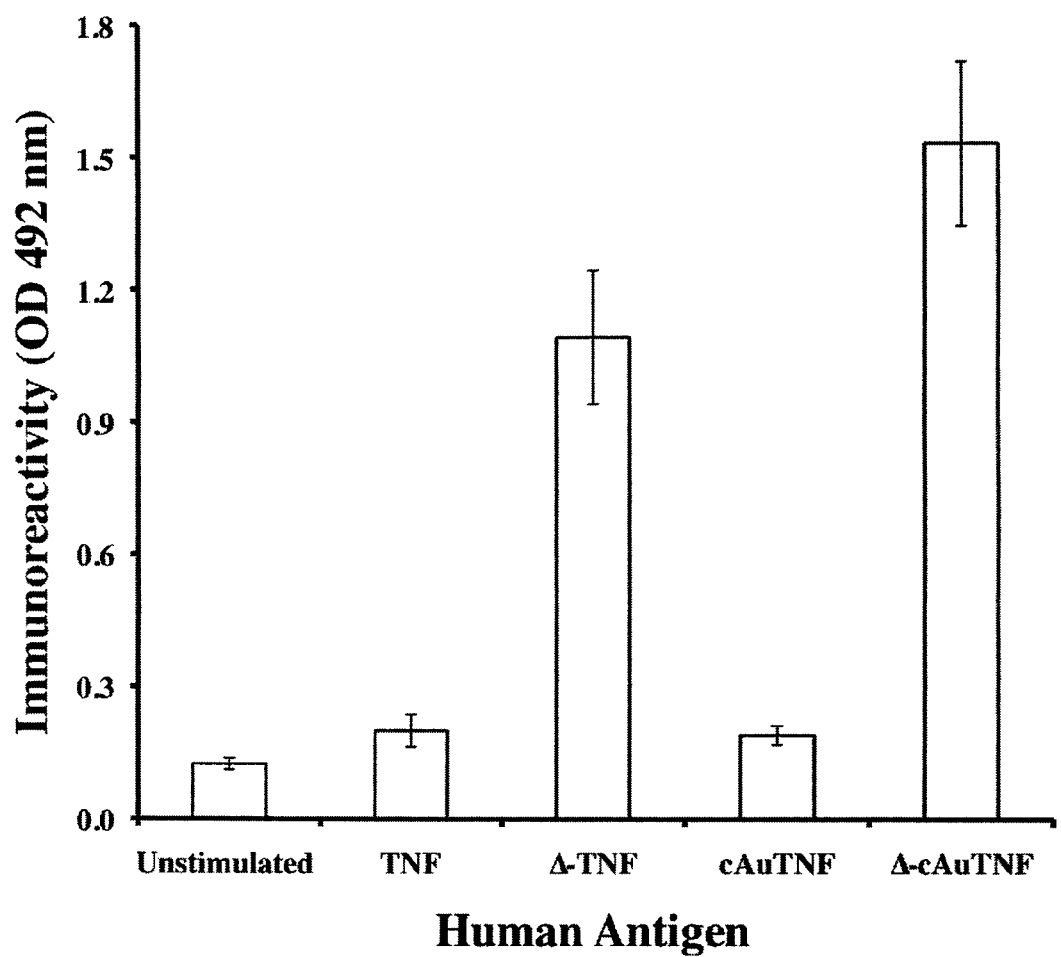
FIG. 5A provides data from lymphocytes isolated from five separate donors showing that only the lymphocytes immunized with the heat-denatured preparations of TNF or heat denatured colloidal gold bound TNF successfully generated a human anti human TNF antibody response.

B-cell/monocytes were co-cultured with various forms of the heated denatured human TNF antigens. Native TNF preparations (i.e., those not heat denatured) were used as controls. The cultures were incubated with the antigens for 7 days (the immunization phase) and subsequently exposed to the various stimuli (CD40L, IL-2 and IL-21; the stimulation phase) to induce class switching. The above culture is a preferred culture developed at CytImmune Sciences, Inc., Rockville, Md. Nevertheless, the use on the denatured antigens should not be limited to this culture system alone. After an additional week of incubation, the supernatants were removed and tested by ELISA for the presence of antibodies that recognize the native antigen. The data from lymphocytes isolated from five separate donors is shown in FIG. 5A. Briefly, the data presented in FIG. 5A show that only the lymphocytes immunized with the heat-denatured preparations of TNF (soluble or colloidal gold bound) successfully generated a human anti human TNF antibody response.

The data shown in FIG. 5B illustrates the differential cytokine response of the immunized culture to either native TNF or the heat denatured TNF antigens. As discussed above, these data also demonstrate potential points of control with agonists and antagonists.

Example 4

Generation of Human Antibody Response to *Clostridium Difficle* Toxins A&B

Figure 4A:
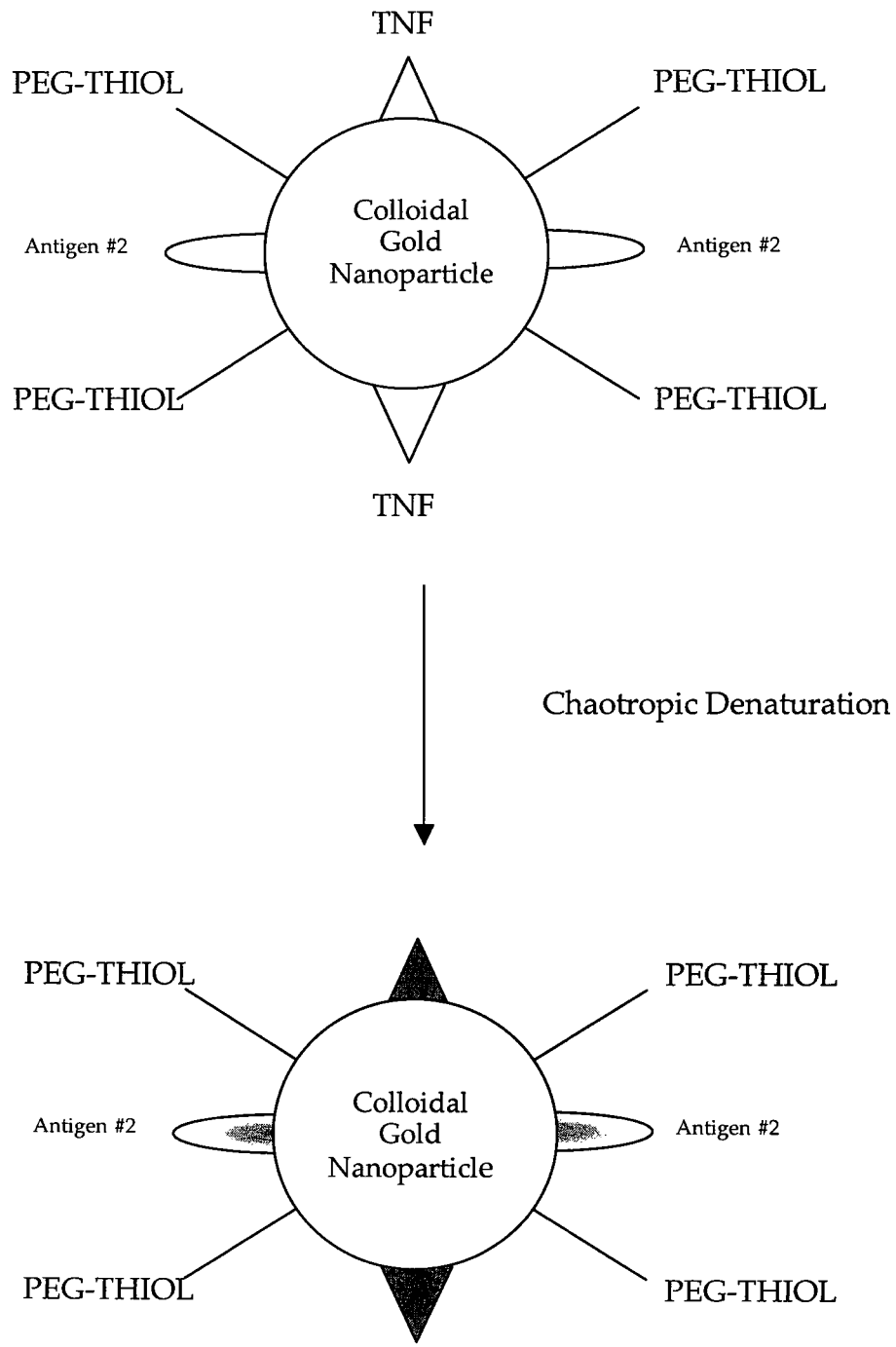
FIG. 4A provides a schematic presentation of the generation of a human TNF/second human antigen chimera on a colloidal gold nanoparticle. The shaded antigens on the bottom of the figure represent the denatured antigens.
Figure 4B:
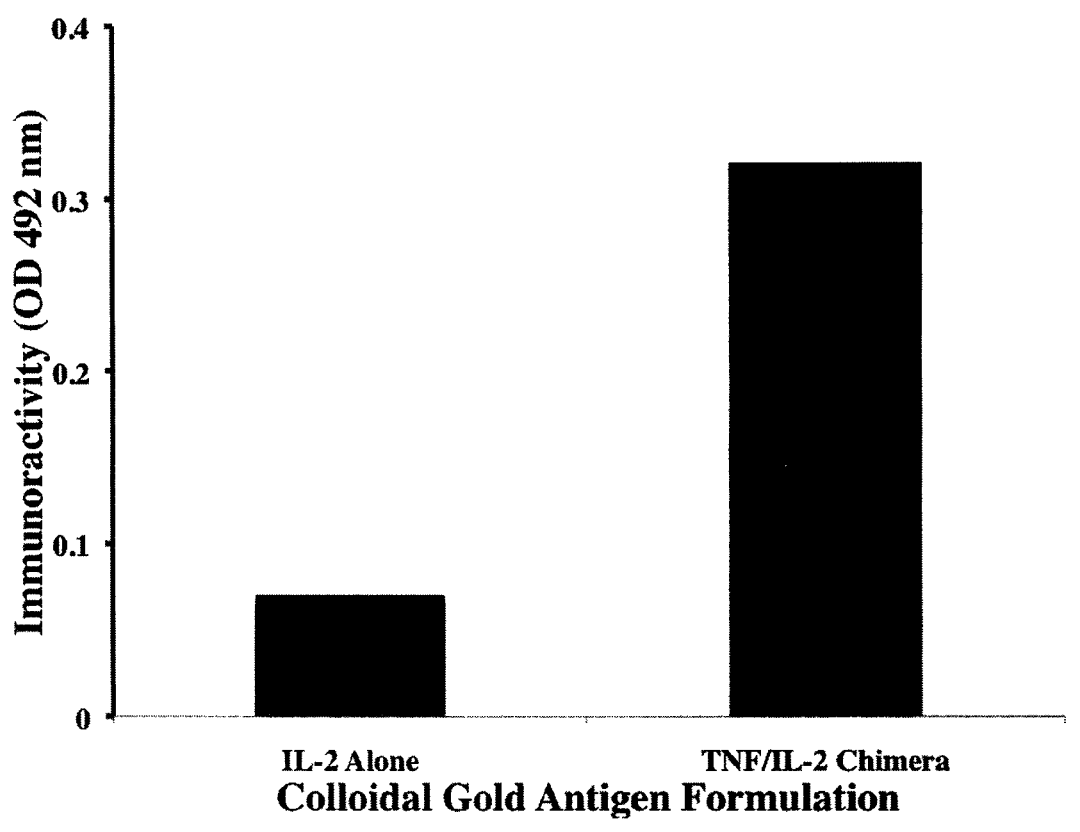
Figure 6:
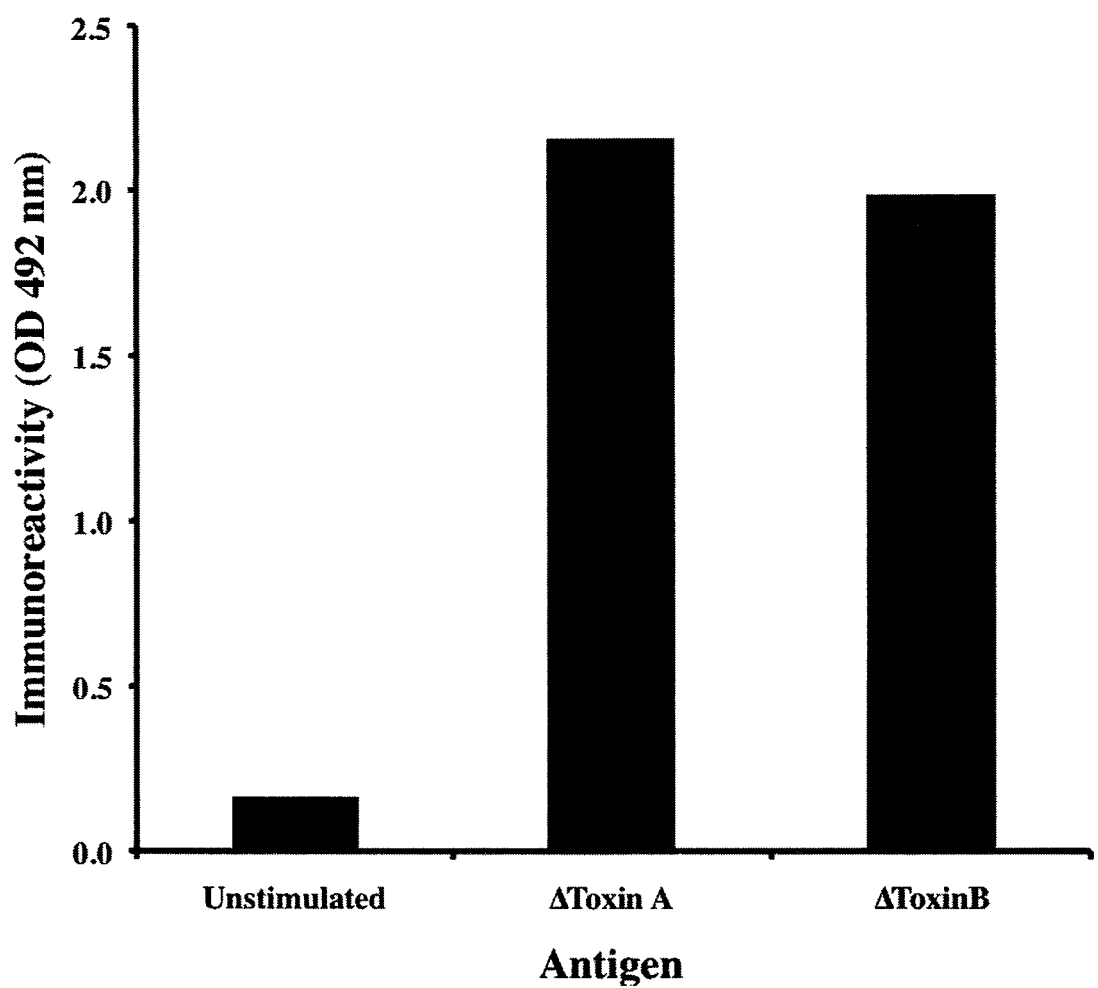
FIG. 6 provides data from lymphocytes isolated from two separate donors showing that only the lymphocytes immunized with the heat-denatured preparations of *C. dif* toxin A or heat-denatured preparations of *C. dif* toxin B successfully generated a human antibody response against the respective immunizing antigen.

B-cell/monocytes were co-cultured with various forms of the heated denatured *C. Dif* Toxin antigens. Native TNF preparations (i.e., those not heat denatured) resulted in cell death. The cultures were incubated with the denatured antigens for 7 days (the immunization phase) and subsequently exposed to the various stimuli (CD40L, IL-2 and IL-21; the stimulation phase) to induce class switching. After an additional week of incubation, the supernatants were removed and tested by ELISA for the presence of antibodies that recognize the native antigen. The data from lymphocytes isolated from two separate donors is shown in FIG. 4A. Briefly these data presented in FIG. 6 show that only the lymphocytes immunized with the heat-denatured preparations of *C. Dif* toxins successfully generated a human anti human toxin antibody response.

Example 5

Generation of Human-Anti-Human EGF Antibody Response

Figure 7A:
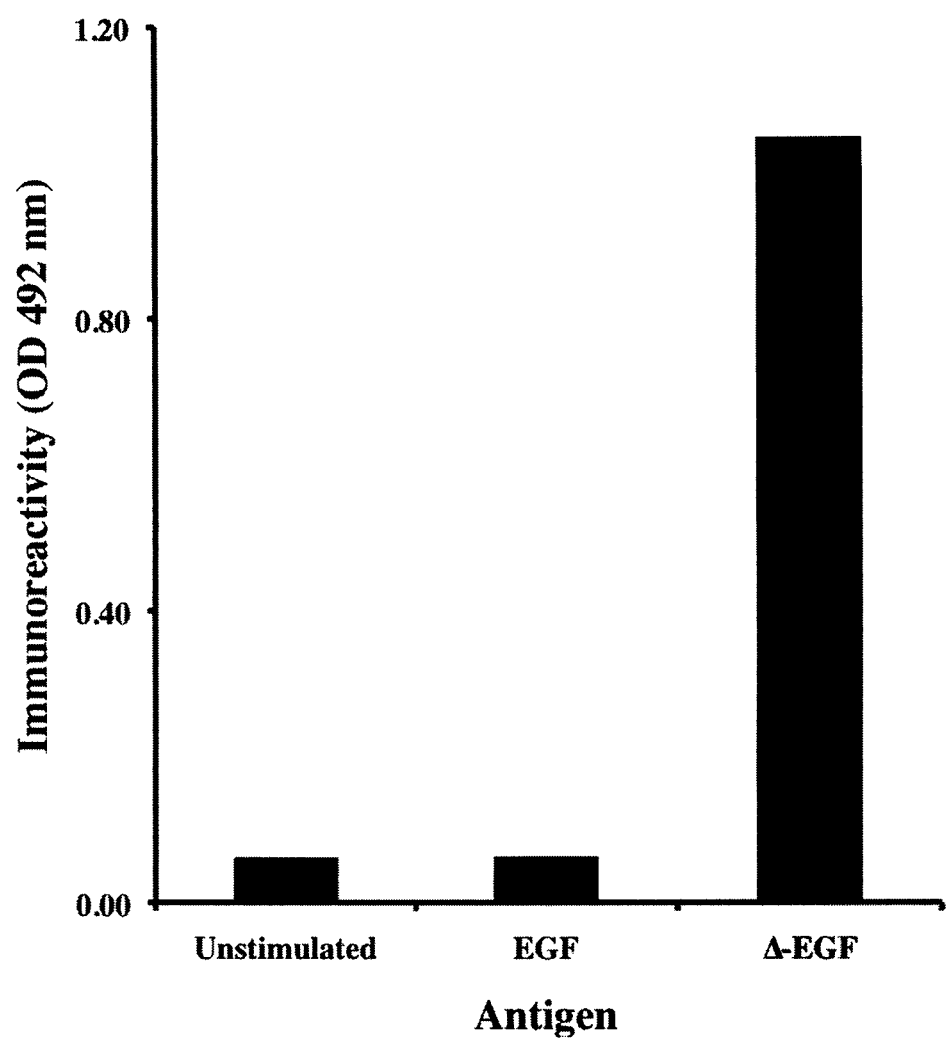
FIGS. 7A and 7B provide data from lymphocytes isolated from two separate donors showing that only the lymphocytes immunized with the heat-denatured or colloidal gold bound (non-denatured) preparations of EGF successfully generated a human antibody response against the respective immunizing antigen.
Figure 7B:
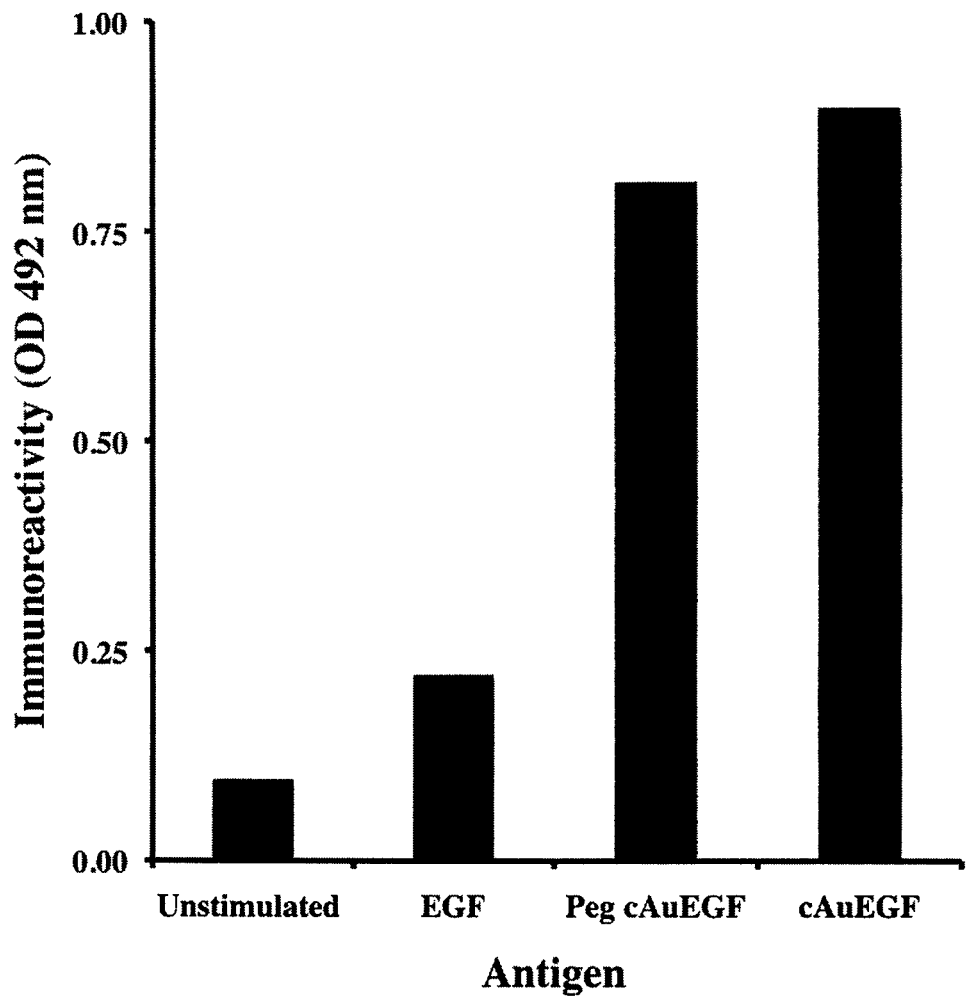

B-cell/monocytes were co-cultured with either the heated denatured EGF or colloidal gold bound EGF antigens. Native TNF preparations (i.e., those not heat denatured) resulted in cell death. The cultures were incubated with the denatured antigens for 7 days (the immunization phase) and subsequently exposed to the various stimuli (CD40L, IL-2 and IL-21; the stimulation phase) to induce class switching. After an additional week of incubation, the supernatants were removed and tested by ELISA for the presence of antibodies that recognize the native antigen. The data from lymphocytes isolated from two separate donors is shown in FIGS. 7A and 7B. Briefly, the data presented in FIGS. 7A and 7B show that only the lymphocytes immunized with the heat-denatured preparations of EGF or the cAuEGF successfully generated a human anti human EGF antibody response.

Example 6

Figure 8:
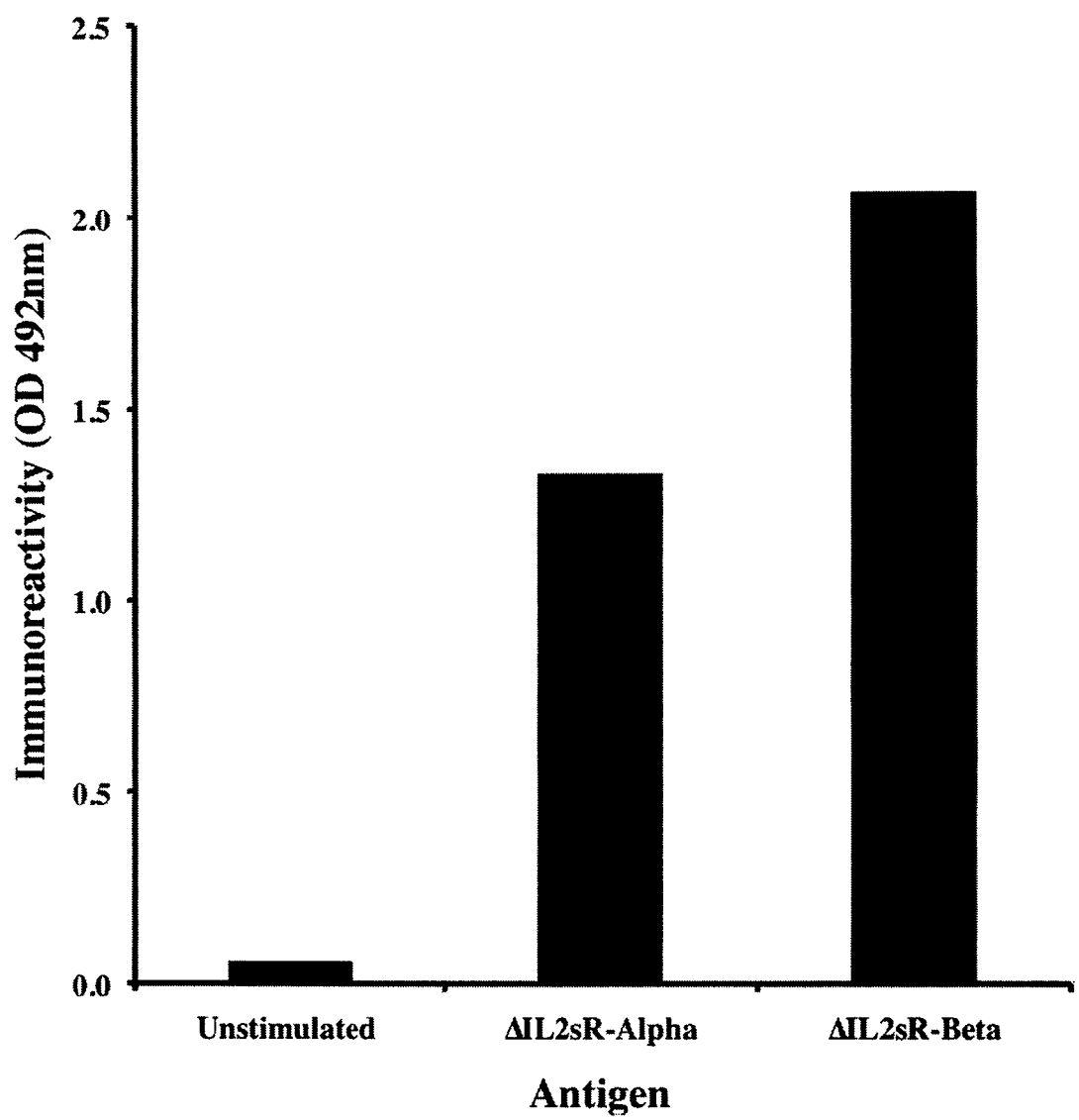
FIG. 8 provides data from lymphocytes isolated from two separate donors showing that only the lymphocytes immunized with the heat-denatured preparations of soluble IL-2 receptor alpha subunit or the soluble IL-2 receptor beta subunit successfully generated a human antibody responses against the respective immunizing antigen.

Generation of Human-Anti-Human Soluble IL-2 Receptor Subunit (α and β) Antibody Response B-cell/monocytes were co-cultured with either the heated denatured soluble IL-2 receptor subunit antigens, alpha and beta. The cultures were incubated with the denatured antigens for 7 days (the immunization phase) and subsequently exposed to the various stimuli (CD40L, IL-2 and IL-21; the stimulation phase) to induce class switching. After an additional week of incubation, the supernatants were removed and tested by ELISA for the presence of antibodies that recognize the native antigen. The data from lymphocytes isolated from two separate donors is shown in FIG. 8. Briefly, the data presented in FIG. 8 show that lymphocytes immunized with the heat-denatured preparations of IL-2 receptor subunits successfully generated human antibody responses to their respective antigen.

Example 7

Control Over the In Vitro Human Antibody Response

The following experiments build upon those presented in Example 3 and were designed to demonstrate control over the class/type of human antibody produced. Thus, following the initial immunization, the stimulation media was changed as indicated in the FIGS. 9, 10, and 11A-11B. As shown in FIGS. 9, 10, and 11A-11B, altering the stimulation media not only induces and controls the strength of class switching from IgM to IgG, but also from IgM to IgA.

Example 8

Generation of Human-Anti-Human TNF mAbs by Classical Hybridoma Technology

Figure 12:
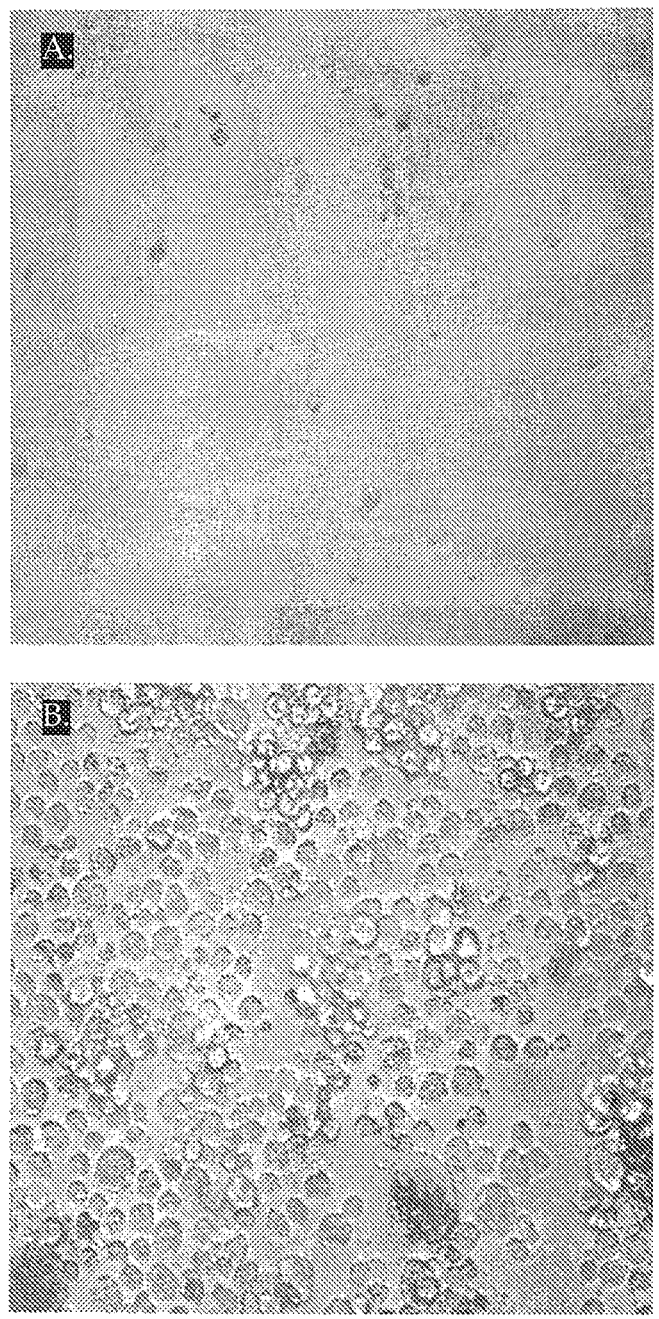
FIG. 12 provides graphic representation of human hybridomas generated from the immunization of human PBLs (unfractionated/unpurified mainly white blood cell preparation) with human TNF antigen. Panel A is hybridoma negative and Panel B is hybridoma positive.

This Example was conducted using the B-cell/monocyte cultures immunized with either the Δ-TNF or Δ-cAu-TNF antigens, or the *C. Dif* antigens. After the initial immunization step, the B-cell/monocyte cultures were incubated with stimulation media. Two weeks after antigen priming, cells were pooled and fused with K6/H6 hetero-myeloma cells using the traditional PEG fusion method described above. Fused cells were then cultured in 96-well plates in selection media containing HAT hybridoma cloning factor and serum containing growth media. Fresh selection media was added weekly. Three weeks after fusion, the presence of growing hybridoma clones was visually documented by digital photography. An example of a hybridoma growing in culture in shown in FIG. 12.

Figure 13:
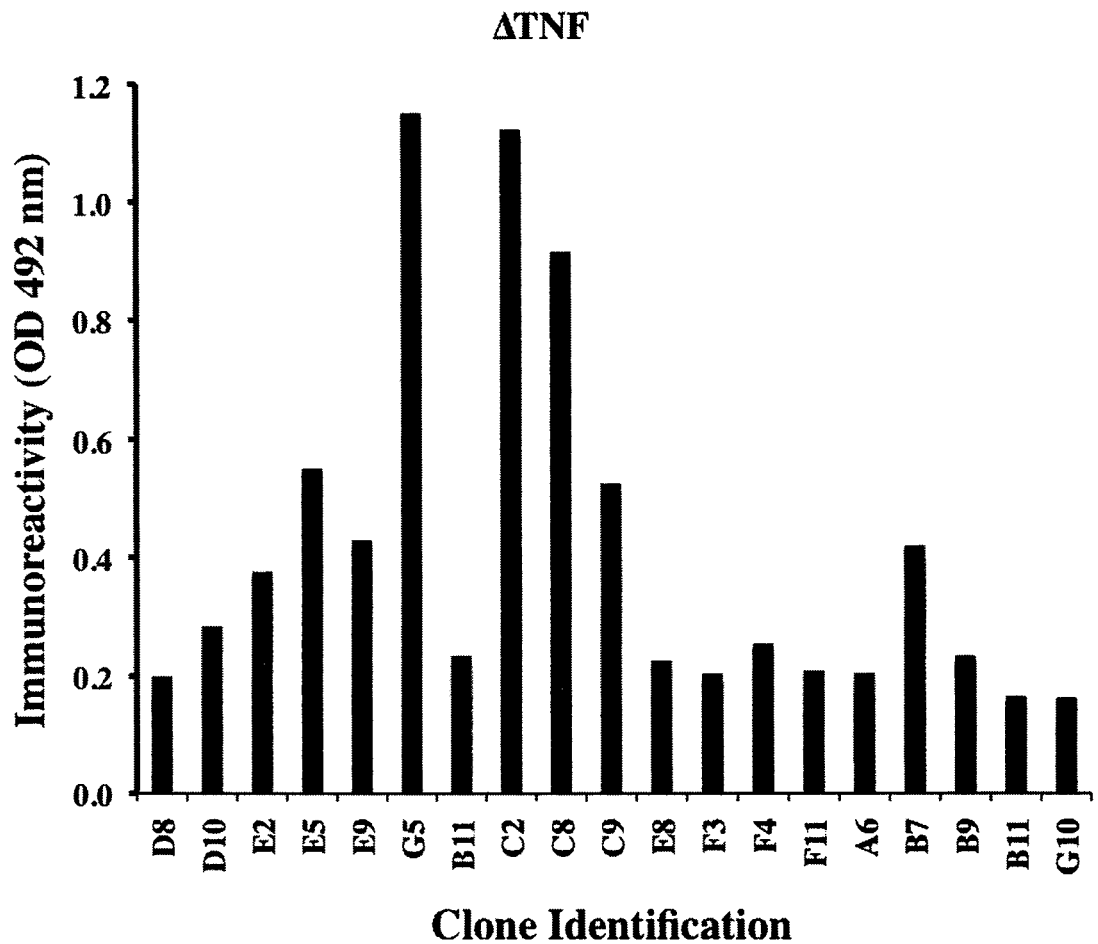
FIG. 13 provides graphical depiction of detection of TNF specific human antibody hybridoma cultures following fusion of the B-cell/monocyte cultures immunized with heat denatured TNF.
Figure 14:
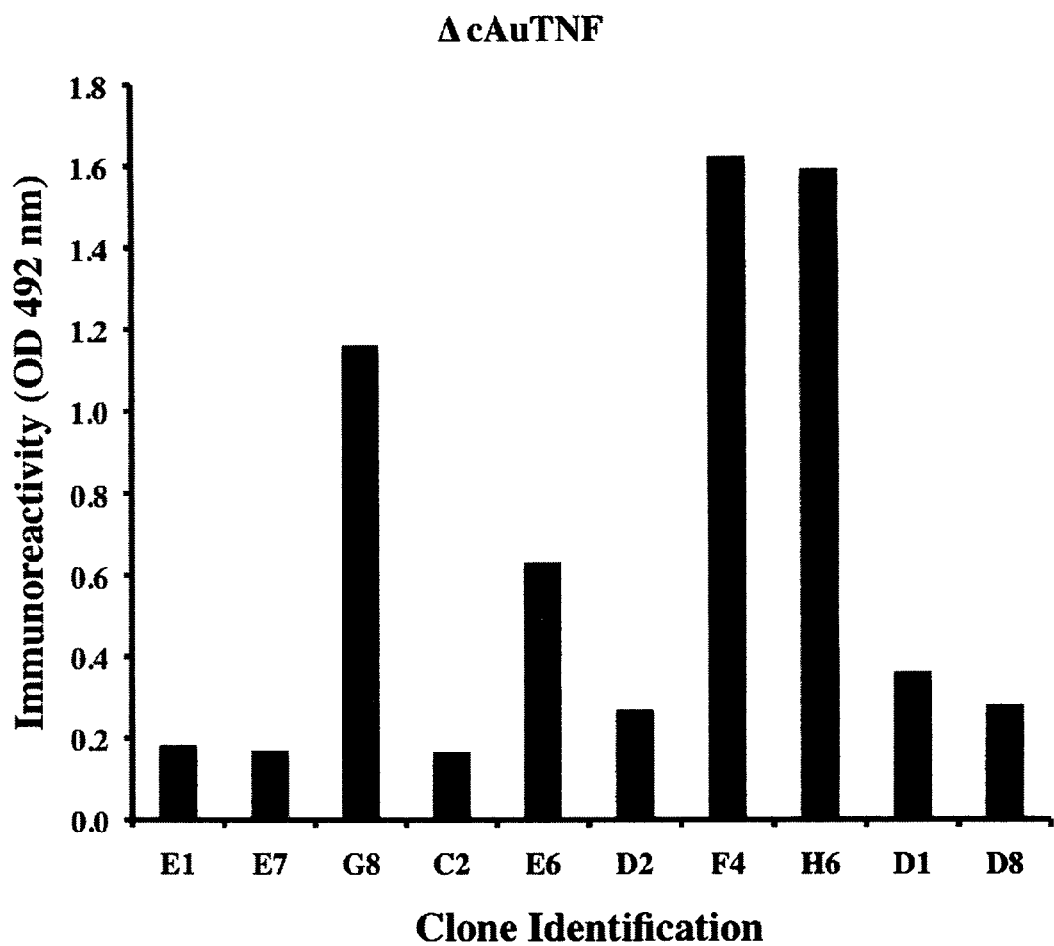
FIG. 14 provides graphical depiction of detection of TNF specific human antibody hybridoma cultures following fusion of the B-cell/monocyte cultures immunized with Δ-cAu-TNF (heat denatured cAu-TNF).
Figure 15:
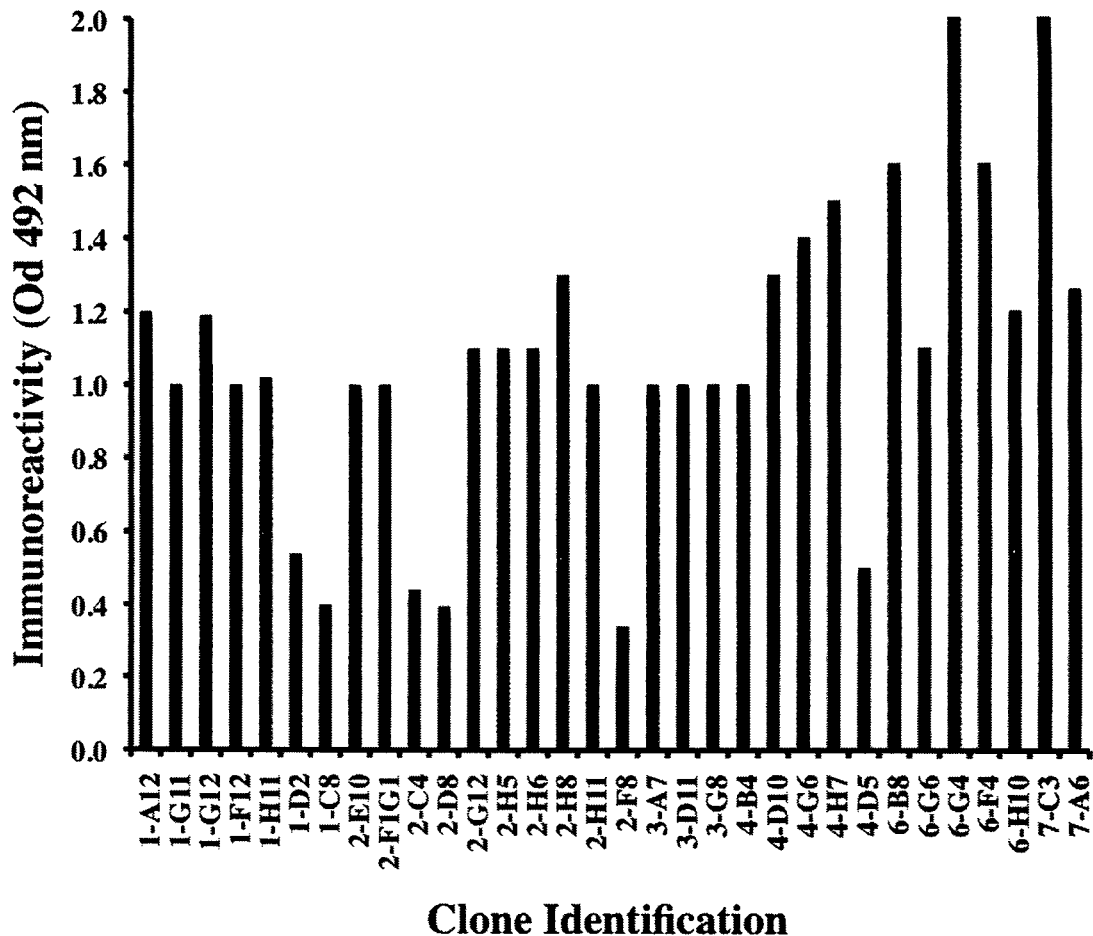
FIG. 15 provides graphical depiction of detection of TNF specific human antibody hybridoma cultures following fusion of the B-cell/monocyte cultures immunized with Δ-*C. Dif* Toxin A.
Figure 16:
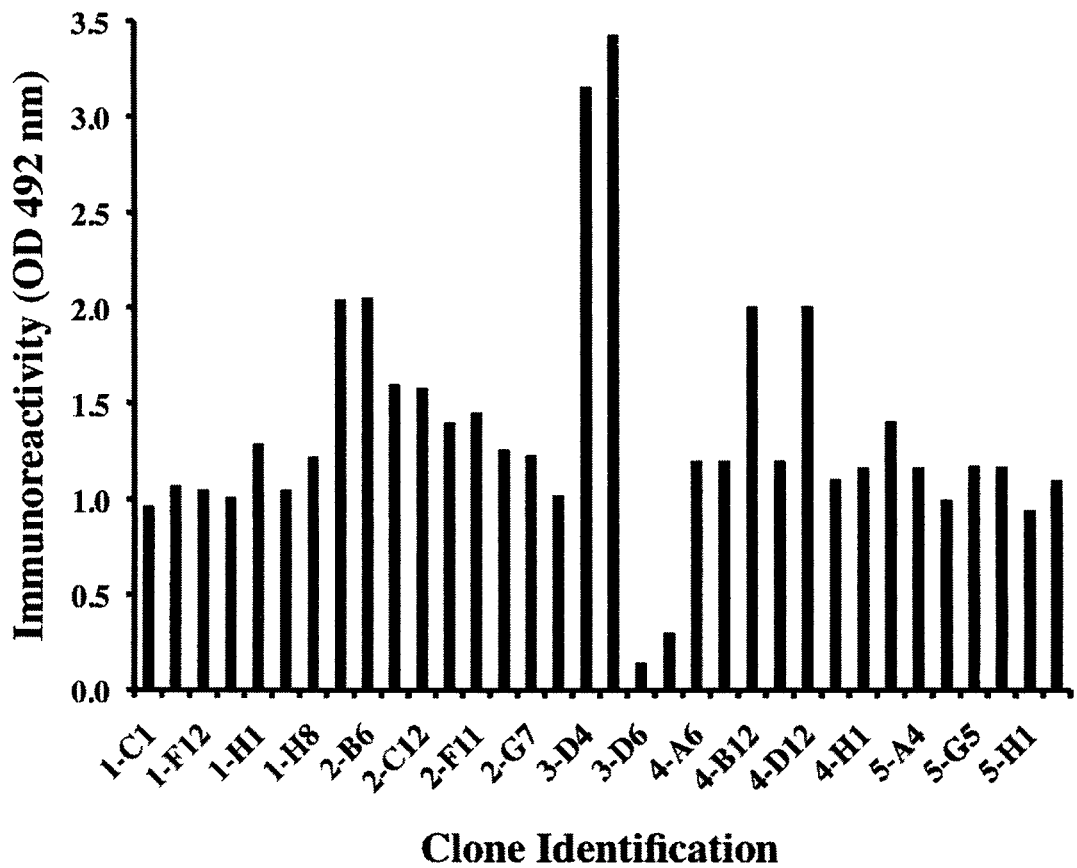
FIG. 16 provides graphical depiction of detection of TNF specific human antibody hybridoma cultures following fusion of the B-cell/monocyte cultures immunized with Δ-*C. Dif* Toxin B.
Figure 17:
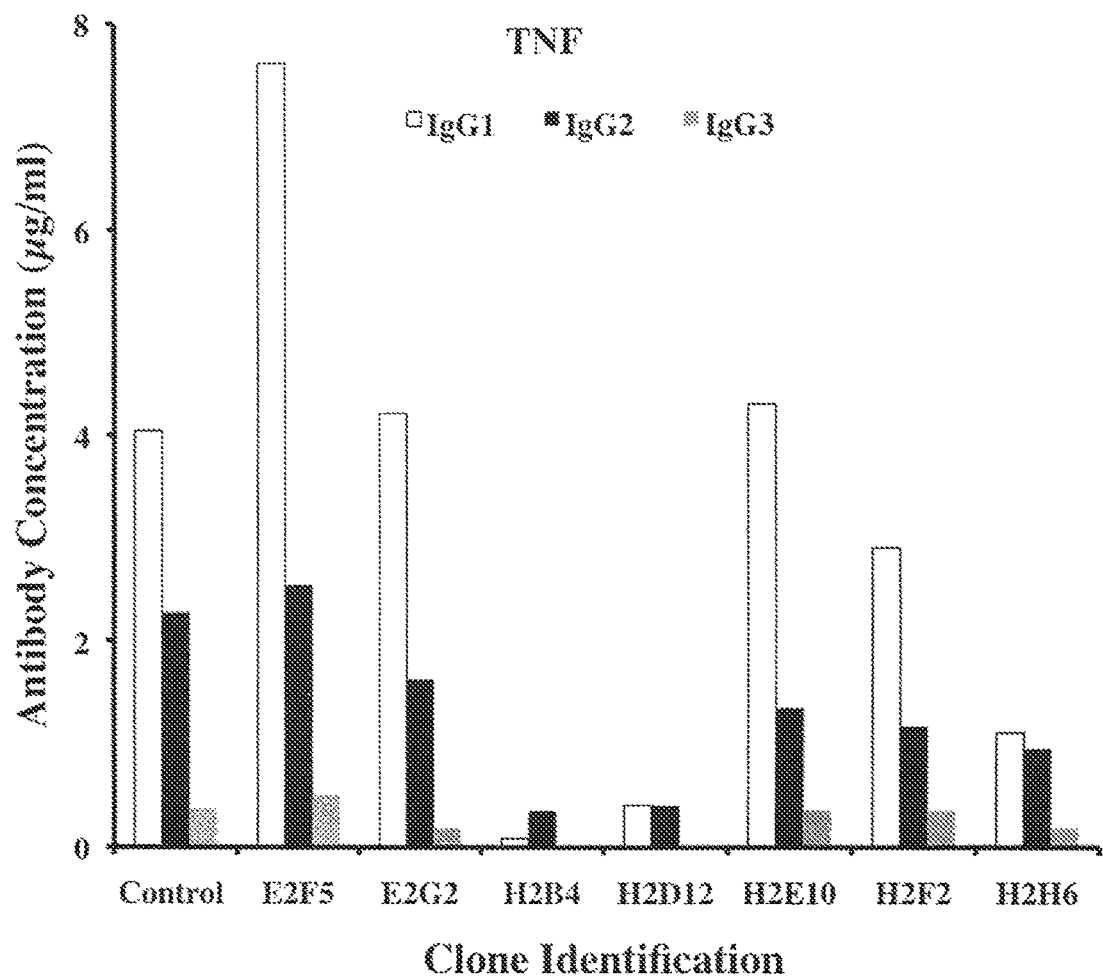
FIG. 17 provides graphical depiction of detection of TNF multiple subclasses of TNF specific human antibodies isolated from hybridoma cultures following fusion of the B-cell/monocyte cultures immunized with ΔTNF (heat denatured cAu-TNF).

In this particular Example, actively growing clones were generated using both the Δ-TNF or Δ-cAuTNF antigens that recognize the native antigen (FIGS. 13-14). Similar responses were noted with the denatured *C. Dif* antigens (FIGS. 15-16).

Example 9

Generation of Fully Human Monoclonal Antibodies of Different Specificities

Figure 18:
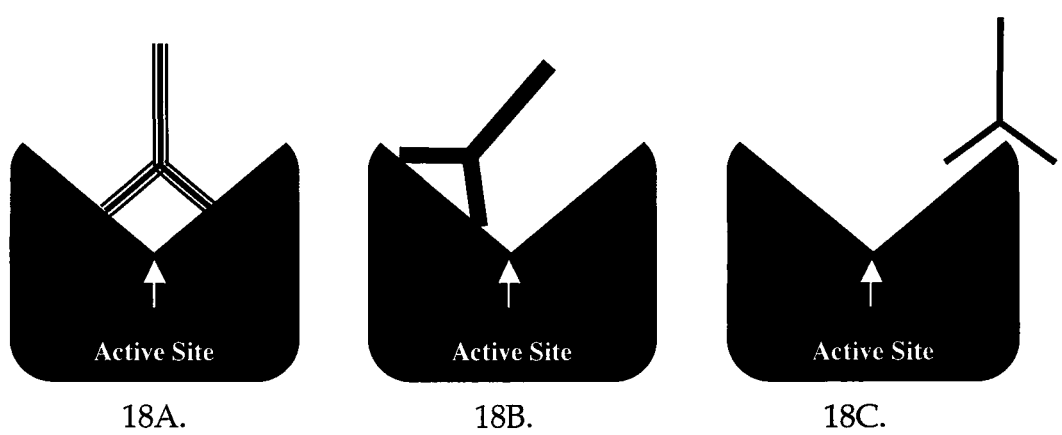
FIG. 18 provides a graphic representation of the generation of fully human monoclonal antibodies with different functionalities.

FIG. 18 shows the generation, developed through the invention, of three fully human monoclonal antibodies to a putative human antigen with different specificities. More specifically, FIG. 18A shows the antibody binds to the active site and either induces activation or inhibition of the wild type antigen. FIG. 18B shows the antibody binds to a site other than the active site and prevents antigen from binding and signaling through the receptor. FIG. 18C shows the antibody does not bind to the receptor at a site other than the active site. Although this particular antibody may not activate or inhibit the receptor, it may be used as a targeting motif It must be noted that, as used in this specification and the claims, the singular forms "a," "an," and "the" include plural referents unless the context clearly dictates otherwise. Thus, for example, reference to a vector composition containing "an agent" means molar quantities of such an agent.

It is to be understood that this invention is not limited to the particular combinations, methods, and materials disclosed herein as such combinations, methods, and materials may vary somewhat. It is also to be understood that the terminology employed herein is used for the purpose of describing particular embodiments only and is not intended to be limiting.

The invention claimed is:

1. A method for producing species-specific antibodies comprising:
co-culturing B cells and antigen presenting cells (APCs) in the presence of a denatured antigen,
generating activated B cells by adding a stimulation media comprising CD40 ligand (CD40L), or an anti-CD40 antibody and one or more of the following cytokine stimuli: a) interleukin-2 (IL-2) and interleukin-21 (IL-21); b) interleukin-5 (IL-5), interleukin-10 (IL-10), and transforming growth factor-beta (TGF-β); c) interleukin-4 (IL-4), interleukin-13 (IL-13), or both IL-4 and IL-13; or d) Interleukin-6 (IL-6);
detecting the production of a species-specific antibody; and
generating a hybridoma from the activated B-cells, wherein the hybridoma produces the species-specific antibodies.

2. The method of claim 1, wherein the B cells and APCs are co-cultured at a ratio of 1:5.

3. The method of claim 2, wherein the denatured antigen is denatured by application of external stress, by application of heat, by the addition of an acid, by the addition of a base, by exposure to a chaotropic agent, by physical stress, or by binding a colloidal metal nanoparticle.

4. The method of claim 3, wherein the denatured antigen is heat denatured by application of heat.

5. The method of claim 4, wherein the denatured antigen is bound to a colloidal metal.

6. The method of claim 5, wherein the colloidal metal is pegylated with a derivatized PEG.

7. The method of claim 6, wherein the derivatized PEG is a thiol PEG derivative.

8. The method of claim 3, wherein the denatured antigen is denatured by binding to a colloidal metal.

9. The method of claim 8, wherein the colloidal metal is pegylated with a derivatized polyethylene glycol (PEG).

10. The method of claim 9, wherein the derivatized PEG is a thiolated PEG derivative.

11. The method of claim 1, wherein the APCs are isolated peripheral blood APCs.

12. The method of claim 1, wherein the antigen is a human self-antigen or a non-human non-self antigen.

13. The method of claim 12, wherein the human self-antigen is derived from nucleic acids, tumor antigens, foreign blood cells, or the cells of transplanted organs.

14. The method of claim 12, wherein the non-human non-self antigen is derived from toxins, bacteria, viruses, protozoa, nucleic acids, tumor antigens, foreign blood cells, or the cells of transplanted organs.

15. The method of claim 1, wherein the antigen is a cytokine.

16. The method of claim 15, wherein the cytokine is a lymphokine, monokine, chemokine, interleukin.

17. The method of claim 15, wherein the cytokine is selected from the group consisting of; interleukin-1, interleukin-2, interleukin-3, interleukin-4, interleukin-5, interleukin-6, interleukin-7, interleukin-8, interleukin-10, interleukin-11, interleukin-12, interleukin-13, interleukin-15, interleukin-16, interleukin-17, interleukin-18, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35, interleukin-36, interleukin-37, interleukin-38, the interferon class including, interferon alpha, beta and gamma, the B7 class of molecules, Type I interferon, Type II interferon, tumor necrosis factor-alpha, or lymphotoxin.

18. The method of claim 1, wherein the antigen is tumor necrosis factor-alpha.

19. The method of claim 1, wherein the antigen is a growth factor.

20. The method of claim 19, wherein the growth factor is selected from the group consisting of; fibroblast growth factor, kerotinocyte growth factor, granulocyte-macrophage colony stimulating factor (GM-CSF), monocyte-macrophage colony stimulating factor, granulocyte colony stimulating factor, epidermal growth factor, vascular endothelial growth factor, nerve growth factor, transforming growth factor-alpha (TGF-a), transforming growth factor-beta (TGF-b), Schwann-cell derived growth factor, nerve growth factor, platelet-derived growth factor, insulin like growth factor 1, insulin like growth factor 2, and glial growth factor.

21. The method of claim 19, wherein the growth factor is epidermal growth factor.

22. The method of claim 1, wherein the antigen is an alpha or beta subunit of an interleukin-2 receptor.

23. The method of claim 1, wherein the stimulation media comprises 11-2, CD40L, and IL-21.

24. The method of claim 23, wherein the species-specific antibody is an IgG species-specific antibody.

25. The method of claim 1, wherein the stimulation media comprises anti-CD40, Il-5, IL-10, and TGF-β.

26. The method of claim 25, wherein the species-specific antibody is an IgA species-specific antibody.

27. The method of claim 1, wherein the stimulation media comprises CD40L, and IL4, or IL-13, or both.

28. The method of claim 27, wherein the species-specific antibody is an IgE species-specific antibody.

29. The method of claim 1, wherein the species-specific antibody is a human species-specific antibody.

* * * * *